(12) United States Patent
Carron et al.

(10) Patent No.: US 10,684,172 B2
(45) Date of Patent: Jun. 16, 2020

(54) SPECTROSCOPIC ASSAYS AND TAGGING

(76) Inventors: Keith Carron, Centennial, WY (US); Shane Buller, Laramie, WY (US); Mark Watson, Laramie, WY (US)

(\*) Notice: Subject to any disclaimer, the term of this patent is extended or adjusted under 35 U.S.C. 154(b) by 0 days.

(21) Appl. No.: 13/819,316

(22) PCT Filed: Aug. 30, 2011

(86) PCT No.: PCT/US2011/049802
§ 371 (c)(1),
(2), (4) Date: Aug. 16, 2013

(87) PCT Pub. No.: WO2012/030870
PCT Pub. Date: Mar. 8, 2012

(65) Prior Publication Data
US 2013/0316467 A1    Nov. 28, 2013

Related U.S. Application Data

(60) Provisional application No. 61/378,383, filed on Aug. 30, 2010, provisional application No. 61/418,540, (Continued)

(51) Int. Cl.
*G01N 33/536* (2006.01)
*G01J 3/44* (2006.01)
(Continued)

(52) U.S. Cl.
CPC ........... *G01J 3/4406* (2013.01); *G01J 3/06* (2013.01); *G01J 3/44* (2013.01); *G01N 21/65* (2013.01);
(Continued)

(58) Field of Classification Search
CPC ......... G01N 33/5434; G01N 33/54333; G01N 27/745; G01N 2446/00; G01N 33/54326;
(Continued)

(56) References Cited

U.S. PATENT DOCUMENTS

2002/0162798 A1\* 11/2002 Johnson et al. ............ 210/660
2005/0142567 A1\*  6/2005 Su et al. .................... 435/6
(Continued)

OTHER PUBLICATIONS

PCT International Search Report dated Jan. 18, 2012 in reference to co-pending International Application No. PCT/US2011/049802 filed Aug. 30, 2011.

*Primary Examiner* — Christopher L Chin
(74) *Attorney, Agent, or Firm* — FisherBroyles, LLP; Thomas J. Osborne, Jr.

(57) ABSTRACT

A spectroscopic assay is provided. The assay comprises: a motive particle configured to move within a solution, the motive particle comprising a first analyte binding reagent for selectively binding to a target analyte; and a spectroscopic reporter particle configured to provide a predetermined spectroscopic signal in response to being interrogated by a spectrometer, the spectroscopic reporter particle comprising a second analyte binding reagent for selectively binding to the target analyte, wherein the motive particle and the spectroscopic reporter particle are configured to provide a sandwich assay in the presence of the target analyte via the first and second analyte binding reagents.

15 Claims, 27 Drawing Sheets

Reagent 2 – Floating Particle

Reagent 1 – Spectroscopic Reporter

Related U.S. Application Data filed on Dec. 1, 2010, provisional application No. 61/450,123, filed on Mar. 7, 2011.

(51) Int. Cl.
  *G01N 33/543* (2006.01)
  *G01N 21/65* (2006.01)
  *G01J 3/06* (2006.01)

(52) U.S. Cl.
  CPC ......... *G01N 21/658* (2013.01); *G01N 33/536* (2013.01); *G01N 33/54313* (2013.01); *G01N 33/54373* (2013.01); *G01J 2003/062* (2013.01); *G01J 2003/064* (2013.01); *G01N 2201/0612* (2013.01)

(58) Field of Classification Search
  CPC ............ B01J 20/28021; B01J 20/28026; B01J 2219/005; B01J 2219/00587; B01J 2219/00596; B01J 8/1845; B01J 8/1881
  USPC ........................................ 436/518, 525, 526
  See application file for complete search history.

(56) References Cited

U.S. PATENT DOCUMENTS

| | | | |
|---|---|---|---|
| 2005/0221494 A1* | 10/2005 | Natan | 436/56 |
| 2005/0227252 A1 | 10/2005 | Moon et al. | |
| 2006/0240572 A1* | 10/2006 | Carron et al. | 436/524 |
| 2007/0172899 A1* | 7/2007 | Graham et al. | 435/7.21 |
| 2008/0160537 A1* | 7/2008 | Luotola et al. | 435/7.1 |
| 2013/0337455 A1* | 12/2013 | McNaughton | G01N 1/30 435/6.12 |

\* cited by examiner

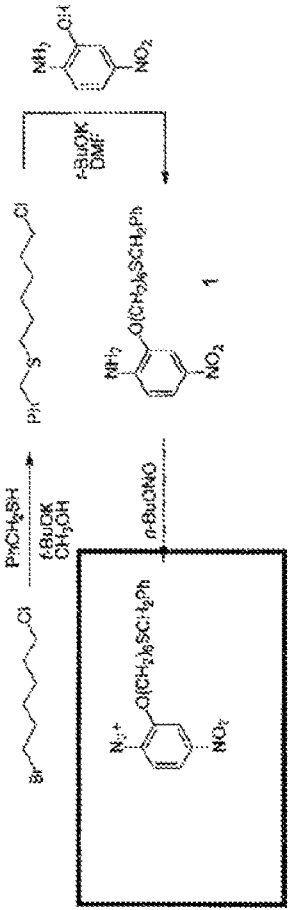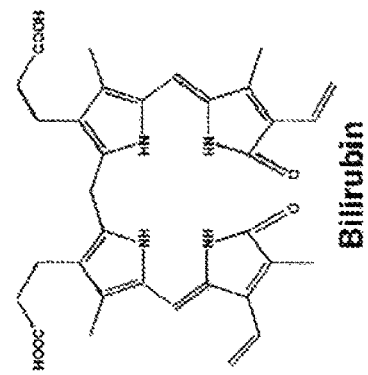
FIGURE 1

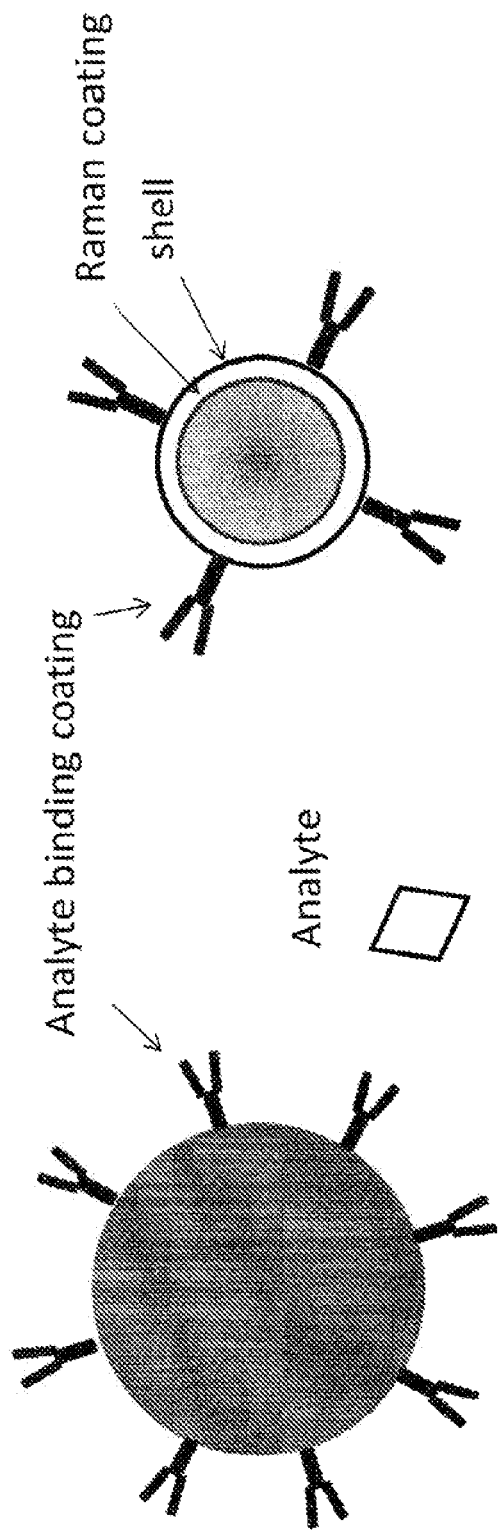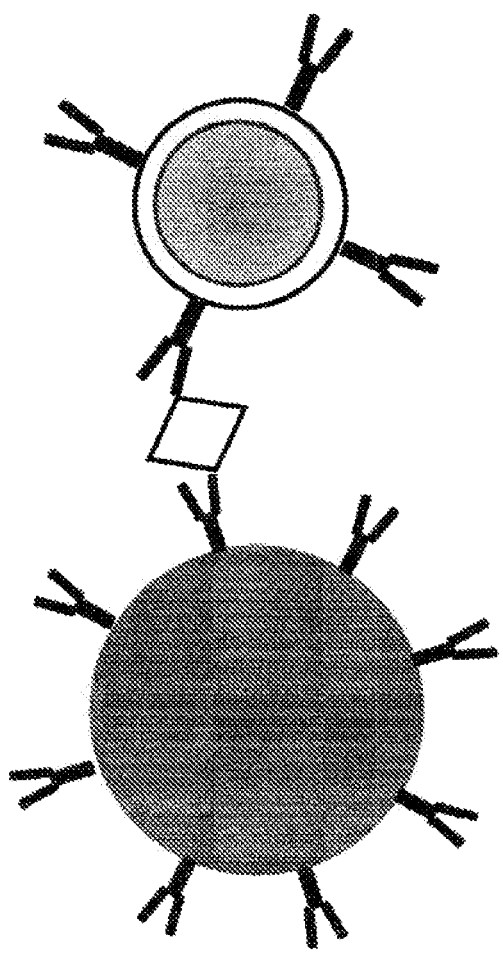
FIGURE 5

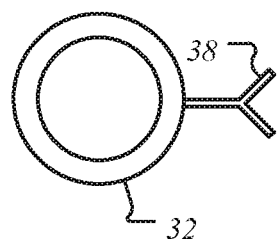
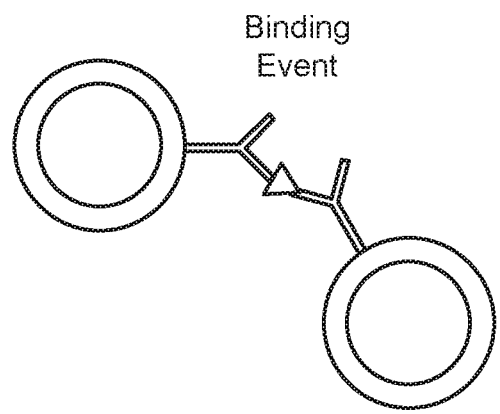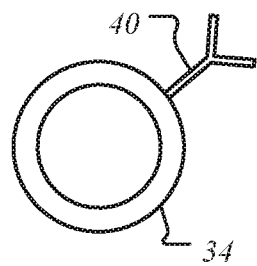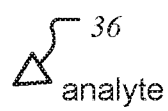
FIG. 8

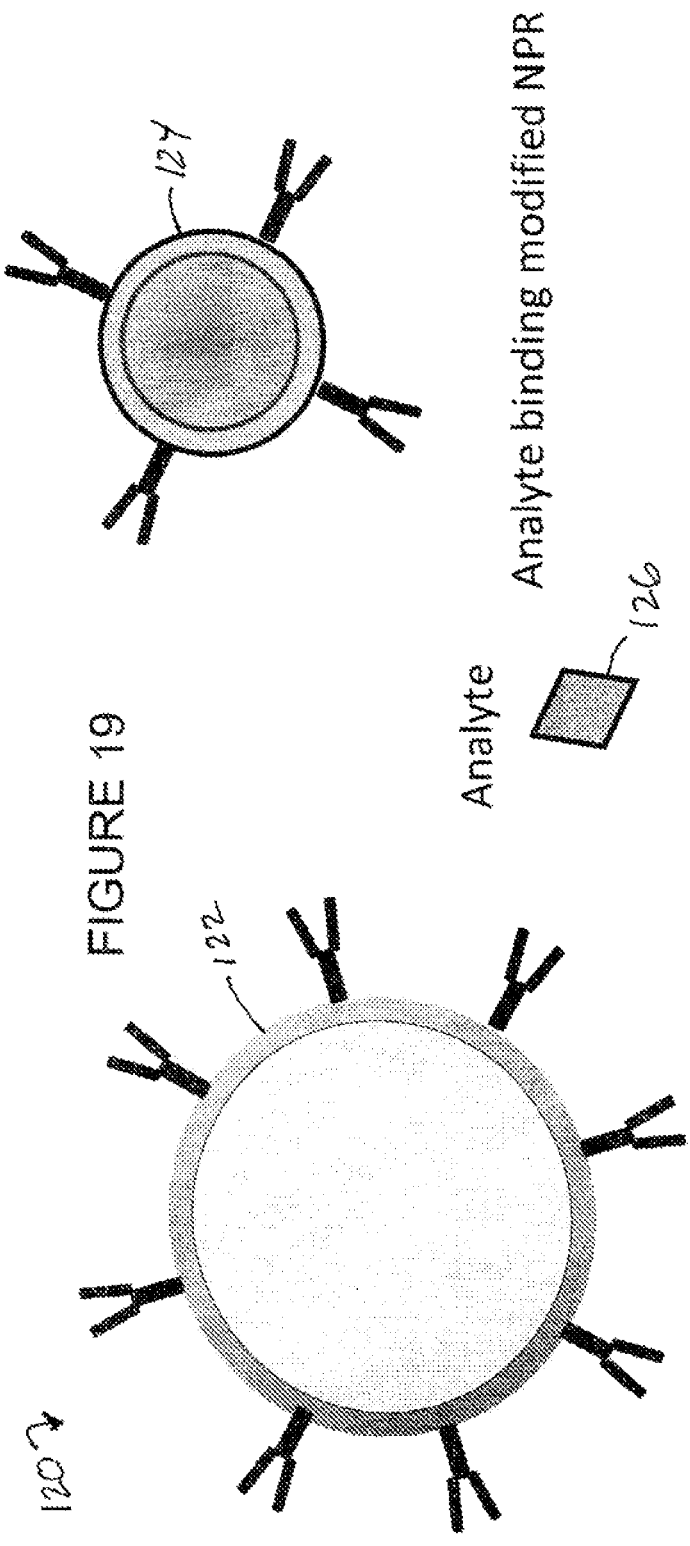

Example of a binding event

Illustration of how particle pairs appear on the surface - curvature is meniscus

SPECTROSCOPIC ASSAYS AND TAGGING

CROSS-REFERENCE TO RELATED APPLICATIONS

This application is a national stage filing under 35 USC 371 of international application number PCT/US2011/049802, dated 30 Aug. 2011, and published on 3 Aug. 2012 under international publication number WO 2012/030870, which claims the benefit of U.S. provisional application No. 61/378,383 filed on Aug. 30, 2010 filed by Carron; U.S. provisional patent application No. 61/418,540 filed on Dec. 1, 2010 by Carron; and U.S. provisional patent application No. 61/450,123 filed on Mar. 7, 2011 by Carron et al. Each of the provisional applications are hereby incorporated by reference as though fully set forth herein.

BACKGROUND OF THE INVENTION a. Field of the Invention

The instant invention relates to spectroscopic assays and tagging.

b. Background

Spectroscopy is often used to analyze samples for their chemical composition. In some cases the sample is pure enough or has a high enough concentration of the material of interest that spectroscopic analysis can be performed directly on the sample. However, it is most often the case that a sample is very impure and the impurities will interfere with the spectroscopic analysis or the constituent that is desired to be detected is at a very low concentration; below the detection limit. The combination of impure sample and low concentration is also common and leads to the most challenging type of spectroscopic analysis.

Some examples of difficult analyses are: water analysis for trace contaminants or pathogens, where the sample may have some degree of purity; or analysis of biological sample where the sample matrix is very complex and the analyte is found at low concentrations. Often in these situations the samples are modified by filtering or a separation technique to enhance the concentration of the analyte or to remove the interfering material from the matrix. These additional steps often require time and expense. It would be desirable to have an analytical technique (assay) that is capable of performing all of these tasks rapidly and at low cost.

In 1999 a paper was published which showed how one could detect trace materials in complex matrices. This paper focused on the detection and quantitation of a metabolite, bilirubin, in biological samples. Bilirubin concentrations in blood or urine are desired as they indicate potential problems with liver function. It is of particular value with neonatal infants who are breaking down their mother's blood to bilirubin before their livers are functioning well enough to remove the toxic material.

In this publication the authors showed how a spectroscopic method known as Surface Enhanced Raman Scattering (SERS) could be used to detect bilirubin which has reacted with a synthetic coating on silver nanoparticles. The coating was synthesized to be highly reactive to the bilirubin molecule. The concept behind this analysis is to place the highly reactive coated SERS into a sample (whole blood) containing metabolic levels of bilirubin and to detect reaction product. The coating is illustrated in FIG. 1.

The authors were able to demonstrate that a small spectral feature was observed due to the reaction product and that peak could be used for quantitation. The spectra and resulting quantitative response curve are illustrated in FIG. 2.

Even though the SERS effect enhances the spectral signal by as much as $10^8$ the spectrum shown in FIG. 2 is dominated by features from whole blood components in the matrix. This interference greatly limits the quantitation of bilirubin in whole blood and prevents the detection of low quantities.

Another limitation to the detection limit of material is the particle nature of SERS. SERS requires nanoparticles of certain metals to be on the order of 100 nm. As the amount of analyte decreases it is necessary to concomitantly decrease the number of particles such that the amount of reacted analyte on the surface is high. Or conversely, the equivalent problem is that at low concentration the number of particles with a reacted bilirubin on the surface becomes small compared with those without a bilirubin. In either case, this situation is illustrated in FIG. 3. The sample will contain many particles that are not in the laser beam, and therefore, they are not detected.

This limit is fundamental. One cannot simply use a larger laser beam to interrogate more particles. The size of the laser beam is related to the spectral resolution. This is illustrated in FIG. 4. A spectroscopic analyzer, in the illustration we show the common Czerny-Turner design, produces a spectral resolution that is related to several factors, one of which is the aperture width, w. As w becomes larger the spectral resolution becomes worse. The spectral resolution must be sufficient to resolve the analyte spectral feature from the matrix features. The spectral resolution also is a factor in the detection limit as the height of the peak (known as the signal) is decreased with the loss of spectral resolution. This fundamental limit will limit the sensitivity of an assay even in pristine samples.

A solution to this fundamental limit was published as a patent application in 2006 (U.S. patent application Ser. No. 11/211,325) by Canon and Ray. Their method is illustrated in FIG. 5. FIG. 5A illustrates the concept of their paramagnetic pull-down assay. Two particles are used for this assay: a paramagnetic particle and a SERS active nanoparticle. Both particles are modified. The paramagnetic particle is modified with an analyte binding coating. The SERS active nanoparticle is coated with a material that produces a strong Raman signal, a protective coating, such as a $SiO_2$ coating, and an analyte binding coating. The protective coating protects the SERS active nanoparticle and provides a surface to bind the analyte binding coating.

Figure illustrates the result of a positive paramagnetic pull-down assay. The assay results in a "sandwich" composed of a paramagnetic particle, the analyte, and a SERS active nanoparticle. This sandwich will produce a large SERS signal due to the coated SERS active nanoparticle. However, at this step of the assay the sample will always exhibit a large SERS signal since the SERS active nanoparticles are always present. Further, the signal produced will be that of the coating and is not related to the analyte.

FIG. 6 shows steps of a complete paramagnetic pull-down assay 10. The assay begins by adding a sample to a pre-treated vial in operation 12. The pre-treated vial contains the two particle types described in FIG. 5. The particle types may, for example, be in the form of a pellet or a coating on the inside of the vial. The sample is added to the vial in operation 14, and the vial is shaken vigorously to disrupt the particles and mix the particles in a solution with the sample in operation 16. The vial is then gently shaken to ensure that the particles stay suspended and convectively mix with the sample in operation 18. The final step uses a magnet to pull the paramagnetic material to a point in operation 20.

FIG. 7 demonstrates the significance of an invention described in 2006 U.S. patent application Ser. No. 11/211, 325 by Carron and Ray (the '325 application), which is incorporated herein by reference in its entirety. In a system described in the '325 application, the pellet produced by a magnetic pull-down will only contain SERS active particles if the analyte is present to create the sandwich shown in FIG. 5B. The pull-down removes the particles from the sample matrix to effectively remove interferences from the matrix and it allows a small laser beam to interrogate all of the assay's SERS active particles that are indicative of a positive result. This is illustrated in FIG. 7A.

FIG. 7B shows that one could use the sample vial as an internal standard to normalize differences between sample vials or instrumentation to make a globally valid assay. FIG. 7C shows a result of the assay—a calibration curve with accurate predicted concentrations of analyte and a detection limit described by the RDL (Reliable Detection Limit).

If, as shown in FIG. 6, the pre-treated vial contains particles with a plurality of analyte binding coatings and an associated unique Raman coating on the SERS active particles for each analyte specific coating, a multiplex assay is created. A multiplex assay has the advantage of testing for multiple analytes simultaneously. For example, a medical assay for sexually transmitted diseases may contain the particle elements needed to detect several diseases at one time.

BRIEF SUMMARY

A spectroscopic assay is provided. The assay comprises: a motive particle configured to move within a solution, the motive particle comprising a first analyte binding reagent for selectively binding to a target analyte; and a spectroscopic reporter particle configured to provide a predetermined spectroscopic signal in response to being interrogated by a spectrometer, the spectroscopic reporter particle comprising a second analyte binding reagent for selectively binding to the target analyte, wherein the motive particle and the spectroscopic reporter particle are configured to provide a sandwich assay in the presence of the target analyte via the first and second analyte binding reagents.

A multiplex spectroscopic assay is also provided. The multiplex assay comprises: a motive particle configured to move within a solution, the motive particle comprising a first analyte binding reagent for selectively binding to a first target analyte and a second analyte binding reagent for selectively binding to a second target analyte; and a first spectroscopic reporter particle configured to provide a first predetermined spectroscopic signal in response to being interrogated by a spectrometer, the first spectroscopic reporter particle comprising a third analyte binding reagent for selectively binding to the first target analyte, a second spectroscopic reporter particle configured to provide a second predetermined spectroscopic signal in response to being interrogated by the spectrometer, the second spectroscopic reporter particle comprising a fourth analyte binding reagent for selectively binding to the second target analyte, wherein the motive particle and the first spectroscopic reporter particle are configured to provide a first sandwich assay in the presence of the first target analyte via the first and third analyte binding reagents, and the motive particle and the second spectroscopic reporter particle are configured to provide a second sandwich assay in the presence of the second target analyte via the second and fourth analyte binding reagents.

A spectroscopic taggant is provided. The taggant comprises: a motive tag particle configured to move within a solution, the motive particle comprising a bound reporter particle configured to provide a predetermined spectroscopic signal in response to being interrogated by a spectrometer, the motive tag particle further comprising a protective coating to protect the motive particle and the bound reporter particle within the coating.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 1 shows a synthetic coating for a Surface Enhanced Raman Scattering (SERS) that could be used to detect bilirubin which has reacted with the synthetic coating on silver nanoparticles.

FIG. 5 illustrates a paramagnetic pull-down assay (at label A) and a result of a positive paramagnetic pull-down assay (at label B).

FIG. 8 shows an example implementation of particles for an assay.

FIGS. 19 and 20 illustrate an equivalency between an LDW concept and a paramagnetic pull-down assay.

DETAILED DESCRIPTION OF THE INVENTION

Figure 2:
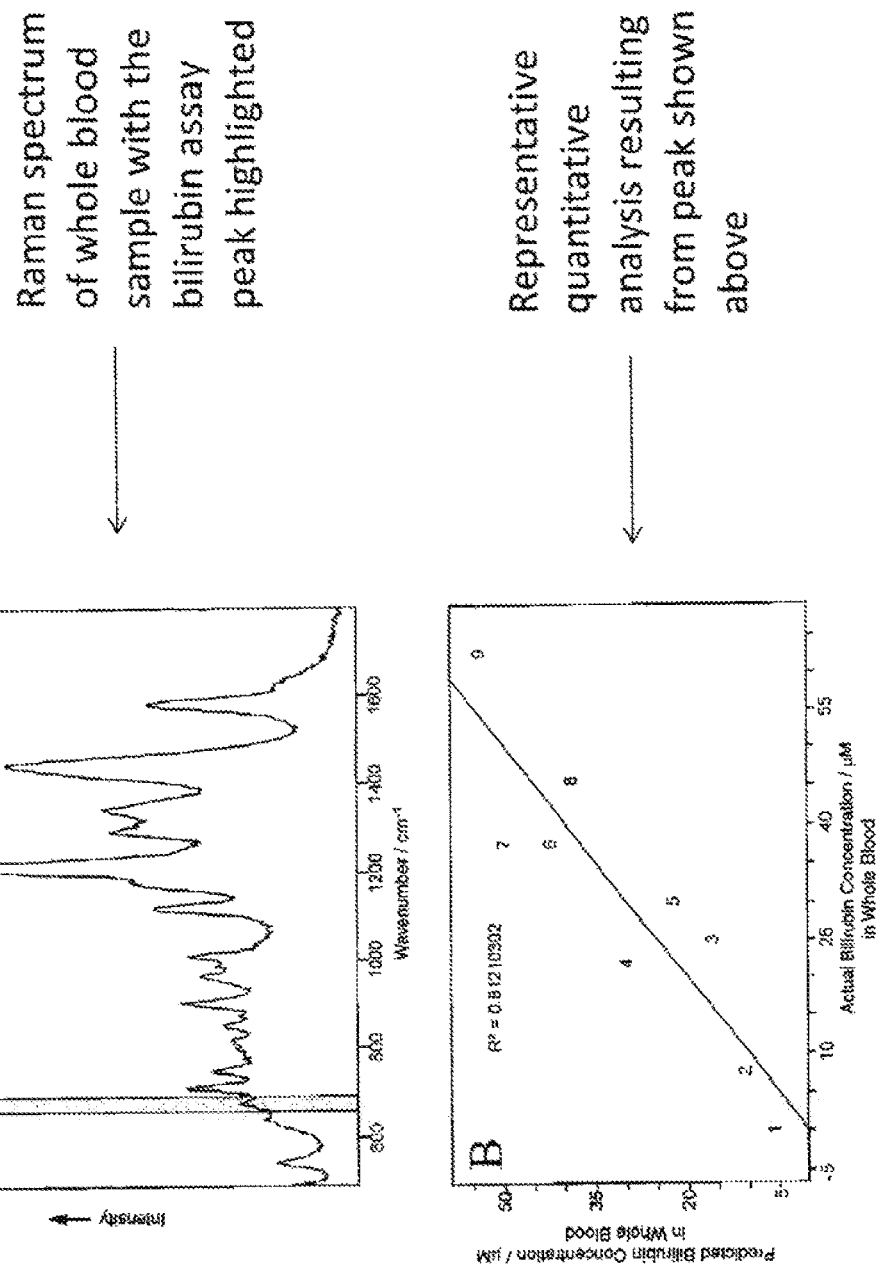
FIG. 2 illustrates a spectrum and a resulting quantitative response curve due to a reaction product and a peak be used for quantitation.

FIG. 8 shows an example implementation of particles for an assay 30. The assay 30 comprises two types of reagents that are configured to interact with a target analyte (e.g., an antigen or antibody of interest). The first reagent comprises a motive particle 32, and the second reagent comprises a spectroscopic reporter particle 34. The motive particles 32 and spectroscopic reporter particles 34 are each configured to bind to the target analyte 36 (e.g., an antigen or antibody) within a solution. In the presence of the target analyte 36, the motive particles 32 and the spectroscopic reporter particles 34 form a sandwich assay in which the target analyte 36 is bound to an analyte binding reagent 38, 40 on both the motive particle 32 and the spectroscopic reporter particle 34, respectively.

In one implementation, for example, the motive particle 38 may comprise a relatively low-density (LD) or high-density (HD) particle. An LD particle for example, comprises a particle having a relatively lower density than a target solution (e.g., lower density than water (LDW) for a water based solution). An HD particle, however, comprises a particle having a relatively higher density than a target solution (e.g., higher density than water (HDW) for an aqueous solution). An LD particle will float in a target solution, and an HD particle will sink in a target solution. Thus, the motive particles can move within a solution by floating or sinking. Alternatively, a motive particle 32 may comprise a neutral density (ND) particle that will stay in solution, and not float or sink within the target solution.

In one implementation, an LD particle, for example, may be formed from a hollow silicon dioxide $SiO_2$ particle. The hollow $SiO_2$ particle, for example, may have a sufficiently low density to provide enough buoyancy to provide a motive force to a completed sandwich assay including the LD particle, a target analyte and a spectroscopic reporter particle. In one particular implementation, for example, a 30 micron or larger $SiO_2$ particle may provide enough buoyancy to provide a motive force for a completed sandwich assay. Similarly, an HD particle can be formed from a solid silicon dioxide $SiO_2$ particle that is sufficiently dense to provide a motive force to sink a completed sandwich assay within a target solution. Similarly, an ND particle can be formed from $SiO_2$ and customized for a particular target solution to provide neutral density in a completed sandwich assay.

The motive particles 32 can include one or more SERS active material (gold, silver, and/or copper). The motive particles, for example, can have SERS active nanoparticles on their surface, SERS active coatings or another method of attaching a SERS active material to the particles. SERS active nanoparticles in solution can aggregate together and fall out of solution, thus decreasing the sensitivity of a SERS assay when the nanoparticles are no longer present in the solution. By "aggregating" the SERS active material on a larger LD, HD or ND particle, the sensitivity of the overall assay can be increased because the greater concentration in one area of the SERS active material. Further, the SERS active material disposed on a motive particle 32 is not as susceptible to clumping and falling out of solution as individual nanoparticles are.

Although particles (whether motive particles 32 or spectroscopic reporter particles 34) are referred to as less-dense-than-water (LDW) or higher-density-than-water (HDW) in example implementations, low density or high density are relative terms and merely refer to being less dense than an intended sample. Thus, a "low density" particle or a "high density" particle may be defined with respect to an intended sample it may be used with. For example, while a given particle may or may not float with regard to an aqueous solution, it may still be less dense than a particular sample, such as whole blood or other more viscous samples. Similarly, while a given particle may not sink with regard to a relatively viscous solution, it may still be denser than another less viscous sample such as an aqueous solution. In other implementations, the particles need not be less-dense than a sample (to float within the sample) or more-dense than a sample (to sink within the sample), but can be designed to other wise move within the sample to move a captured analyte within the sample or away from the sample.

The spectroscopic reporter particles 34 are also configured to bind to the same target analyte (antigen or antibody) as the motive particles 34. The spectroscopic reporter particles 34 also provide a relatively strong recognizable spectroscopic signal so that they may be recognized by a spectrometer. In one implementation, for example, the spectroscopic reporter particles 34 comprise SERS active nanoparticles coated with a material that produces a strong Raman signal, a protective coating, such as a $SiO_2$ coating, and an analyte binding coating. The protective coating protects the SERS active nanoparticle and provides a surface to bind the analyte binding coating.

The motive particles 32 and spectroscopic reporter particles 34 can be adapted to interact with a target analyte by attaching analyte binding reagents to the particles. Where a target analyte 36 is an antigen, for example, the motive particles 32 and spectroscopic reporter particles 34 can be coated or otherwise bound to a plurality of antibodies that are receptors for the target antigen. The coating process, its ability to be an internal standard for a detection process, its ability to protect a surface, and its affinity for an analyte are discussed in U.S. Pat. No. 5,693,152, which is hereby incorporated by reference in its entirety. Exemplary methods for binding antibodies to colloidal particles are described in U.S. Pat. No. 6,770,488, which is also hereby incorporated herein by reference in its entirety. In solution with an antigen, one of the antibodies on the motive particles binds to a site on the antigen. Similarly, one of the antibodies on the spectroscopic reporter particles 34 binds to a different site on the antigen. The two antibodies may be monoclonal antibodies and thereby bind to the same type of site on the antigens. Alternatively, the antibodies may be different monoclonal antibodies or polyclonal antibodies and thereby bind to different sites, or epitopes, on the antigens. Thus, the antigen, which is the analyte in question, creates a coupling of the spectroscopic reporter particle 34 with the motive particle 32, as shown in FIG. 8.

In addition, in some implementations, the motive particles 32 (e.g., LDW particles) and/or the spectroscopic reporters 34 (e.g., SERS active nanoparticle reporters (NPRs)) could be any number of different size particles. The motive particles, for example, could vary depending on the size of the sample. For example, ping pong ball sized or beach ball sized motive particles may be used in larger samples (e.g., within a pool or body of water) that could be easily collected from a surface of the sample. The spectroscopic reporter particles (e.g., SERS active nanoparticles) could have analyte reactive coatings as shown in FIG. 1 for bilirubin or could be bare nanoparticles to natively react with materials. Canon, et al., in U.S. Pat. No. 7,776,610 showed that native SERS active nanoparticles are capable of binding certain materials, such as cyanide or sulfur containing compounds, with very high sensitivity.

Figure 3:
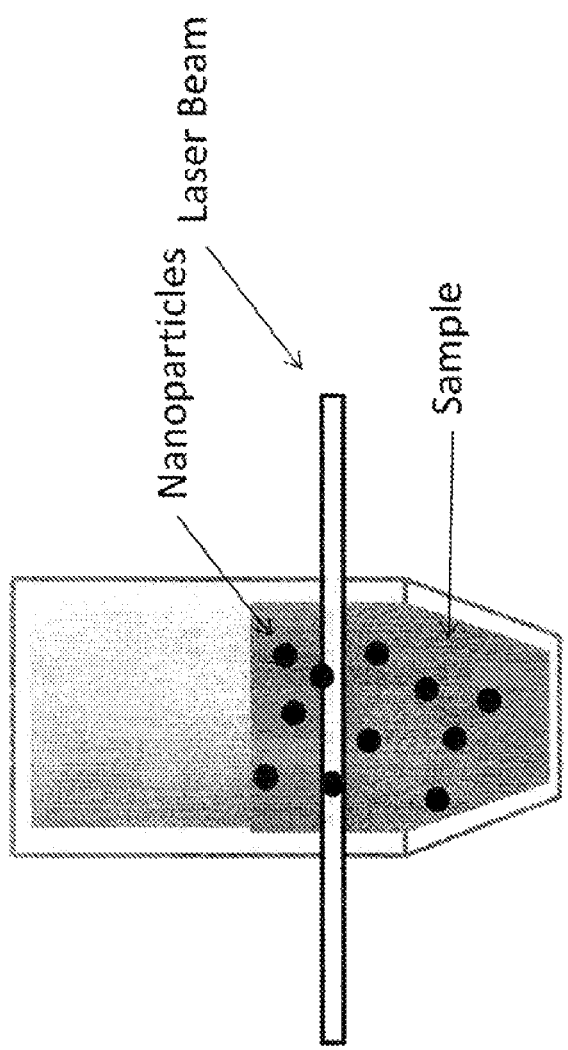
FIG. 3 shows a sample that contains many dispersed particles that are not in a laser beam, and therefore, they are not detected.
Figure 9:
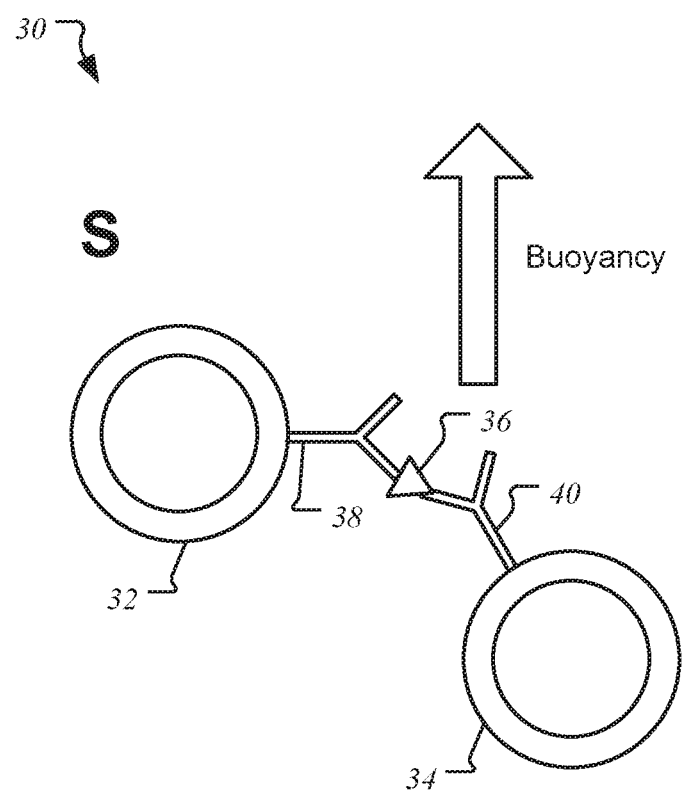
FIG. 9 shows a motive particle moving a sandwich assay including a bound target analyte and a spectroscopic reporter particle within a solution.

FIG. 8 shows a motive particle binding event in which a LD motive particle 32 comprises a low density particle and an analyte reactive coating that selectively binds to a target analyte 26. FIG. 8 also shows a binding event in which a target analyte is bound by at least one motive particle 32 via an analyte binding reagent 38 disposed on the motive particle 32 and is further bound to at least one spectroscopic reporter particle 34 via an analyte binding reagent 40 disposed on the spectroscopic reporter particle 34. As shown in FIG. 9, once bound, the motive particle 32 moves the sandwich assay including the bound target analyte 36 and the spectroscopic reporter particle 34 within a solution. Where the motive particle 32 is buoyant in the solution, for example, the motive particle floats to a surface of the solution, bringing the bound target analyte and spectroscopic reporter with it. Where the motive particle 32 sinks in the solution, the motive particle sinks within the solution, bringing the bound target analyte and spectroscopic reporter with it. Where the motive particle 32 is a neutral density particle in the solution, the motive particle 32 stay within solution and keeps a completed sandwich assay in solution as well. In this implementation, the completed sandwich assay can be detected in a manner similar to that shown in FIG. 3, especially where the spectroscopic reporter particles 34 in the assay provide a relatively strong, identifiable signature.

Figure 10:
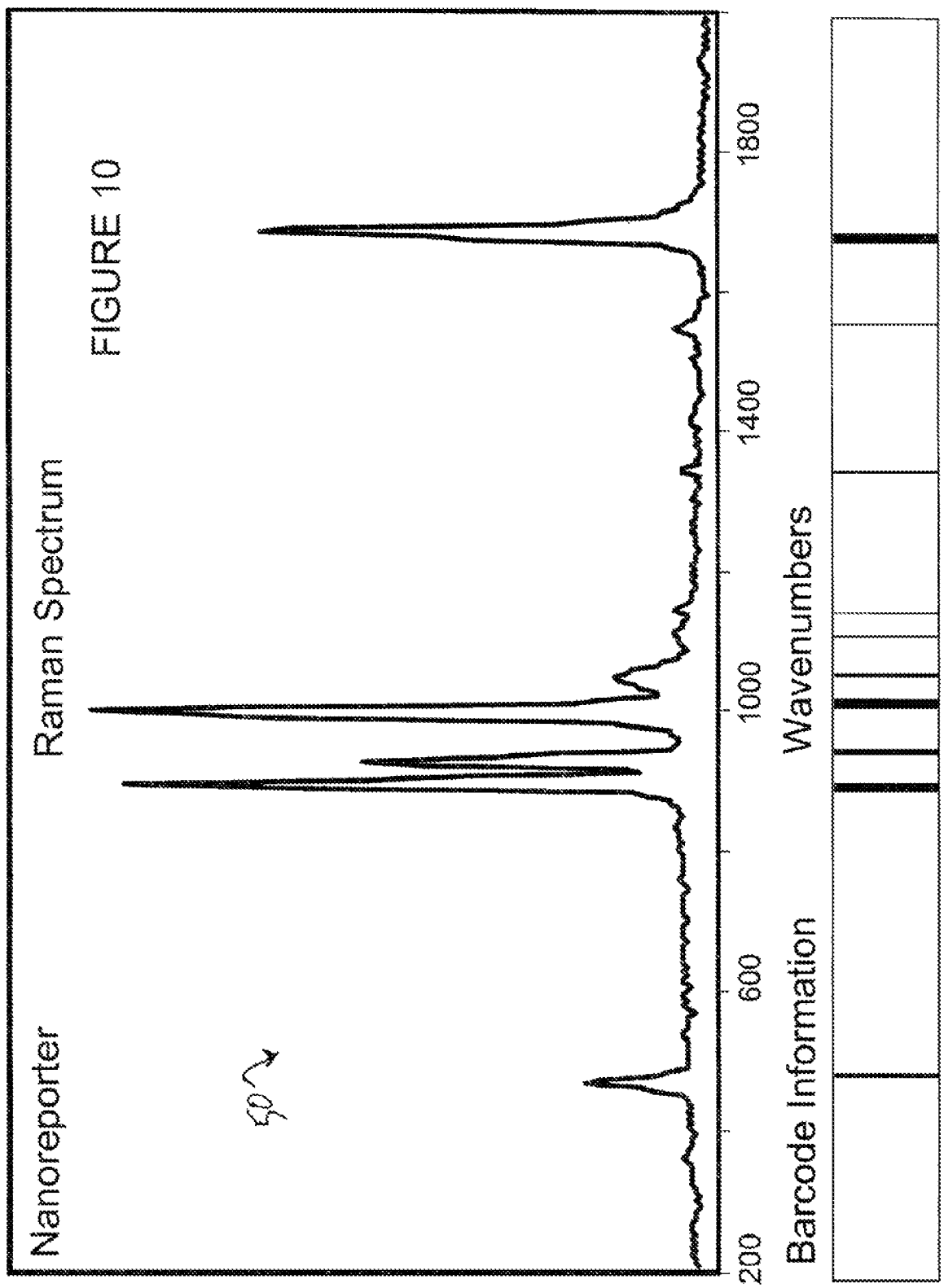
FIG. 10 shows an example spectrum of a SERS active nanoparticle reporter and a corresponding barcode representation of the spectrum of the SERS active nanoparticle reporter.

FIG. 10 shows an example spectrum 50 of a SERS active nanoparticle reporter 34 and a corresponding barcode representation 52 of the spectrum of the SERS active nanoparticle reporter 34. The barcode 52 represents how a complex Raman spectrum can be converted into a simple identification marker much like that used in a retail store. Intense Raman lines are thicker bar, weak line represent thin bars. The location and thickness is determined by the reporter molecule placed on the nanoparticle reporter.

Figure 11:
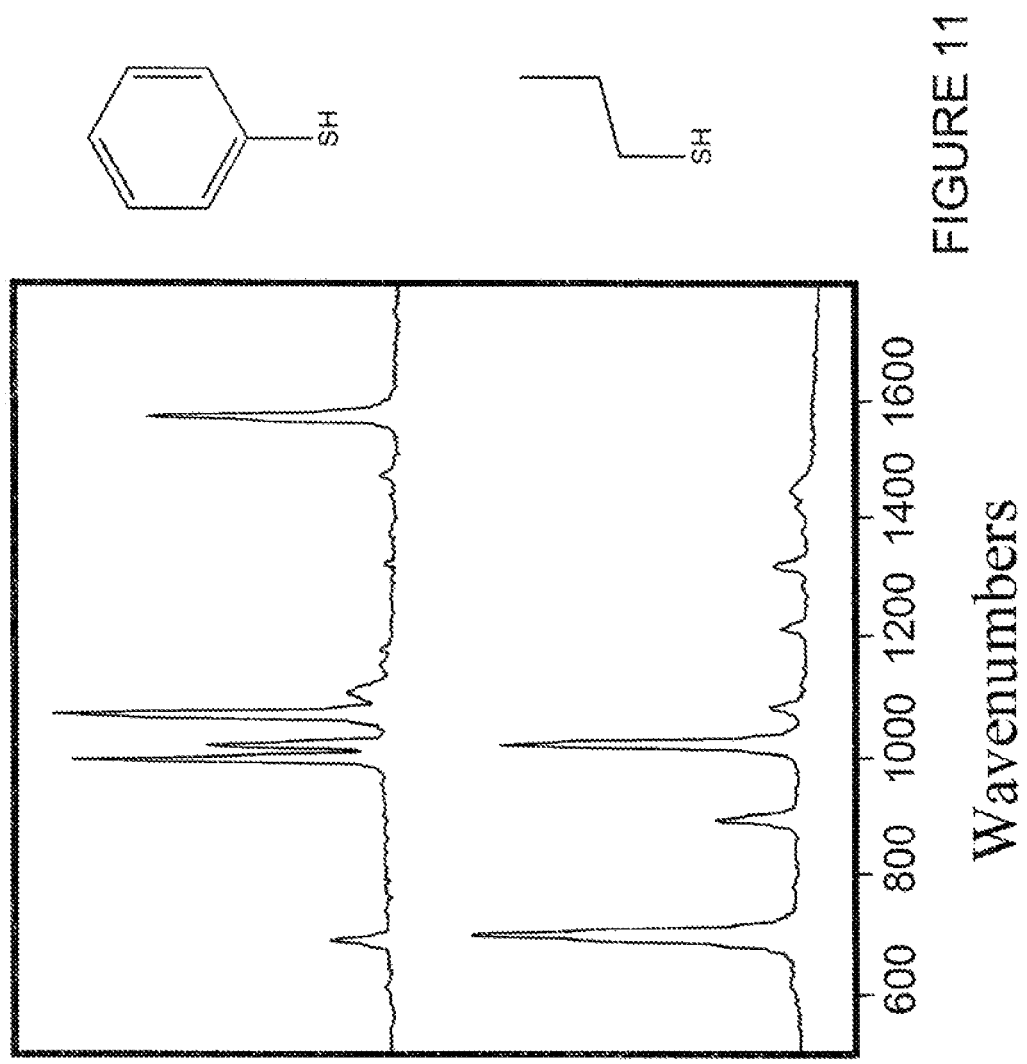
FIG. 11 shows a Raman spectrum of two example SERS active nanoparticle reporters.

FIG. 11 shows Raman spectrum of two example SERS active nanoparticle reporters: benzene thiol and propane thiol.

Figure 12:
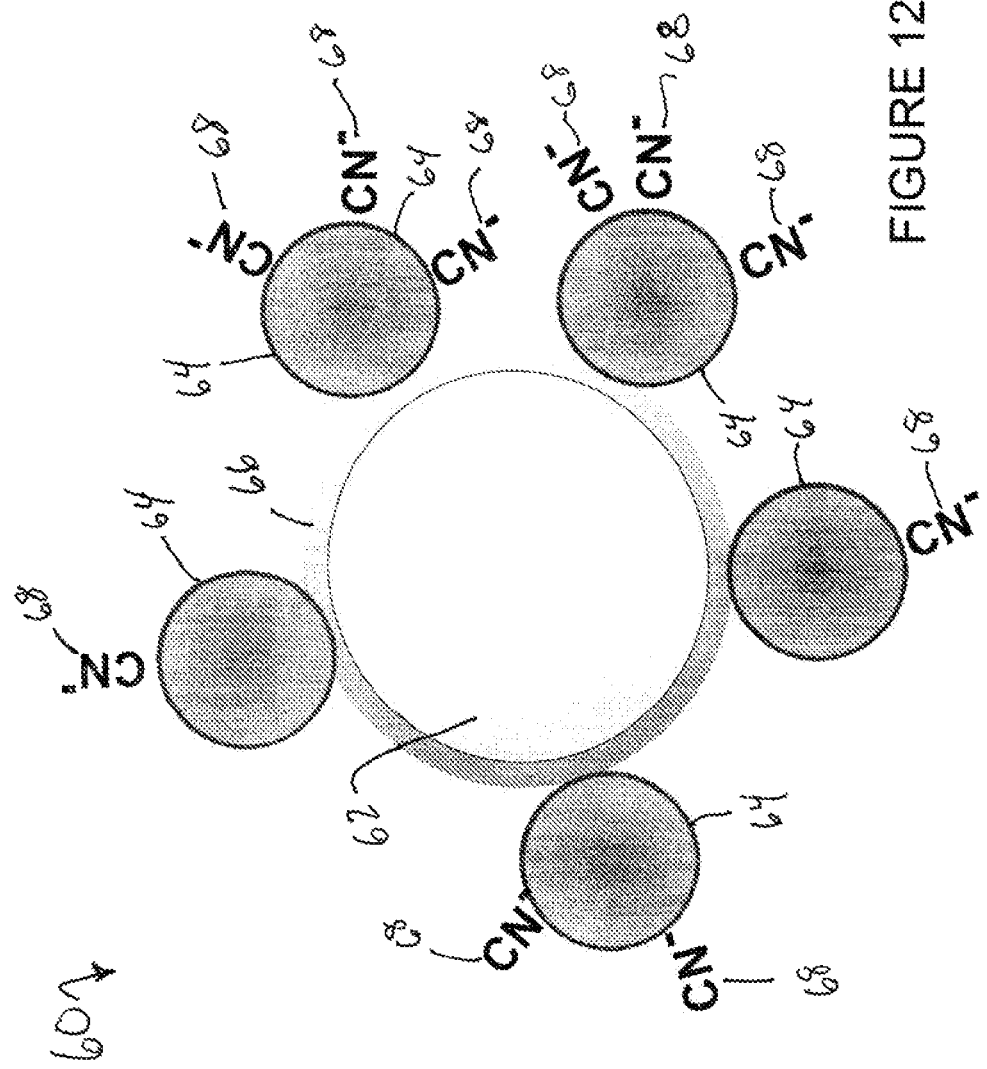
FIG. 12 illustrates an example SERS based approach similar to a paramagnetic pull-down assay.

FIG. 12 illustrates an example SERS based approach disclosed by Carron in U.S. provisional patent application No. 61/378,383 filed on Aug. 30, 2010, which is incorporated herein by reference in its entirety. This approach describes a method 60 similar to a paramagnetic pull-down assay. The advantage is simplicity, efficiency, and application. In this approach, a paramagnetic particle of a paramagnetic assay is replaced with a low density motive particle 62 that can float to the top of a sample (or sink within the sample or remain within the sample). In this implementation, less-dense-than-water (LDW) particles 62 have SERS active nanoparticles 64 (e.g., gold, silver or copper nanoparticles) on their surface 66. In other implementations, however, SERS active coatings or another method of attaching a SERS active material to the particles can be used. As described above, although the particles are referred to as less-dense-than-water (LDW) in this example implementation, low density is a relative term with respect to a targeted sample and merely refers to being less dense than the targeted sample. Thus, a "low density" particle can be defined with respect to an intended sample it may be used with. For example, while a given particle may or may not float with regard to an aqueous solution, it may still be less dense than a particular sample, such as whole blood or other more viscous samples. Also, as described above, the motive particles need not be less-dense than a sample and can be designed to sink or other wise move within the sample to move a captured analyte within the sample or away from the sample.

The SERS active nanoparticles 64 are further coupled to analyte reactive compounds 68 (e.g., coatings or other methods of attaching the compounds to the nanoparticles 64). In this particular example, analyte reactive coatings 68 comprise cyanide compounds bound to the SERS active nanoparticles 64. The SERS active nanoparticles 64 could have analyte reactive coatings as described in FIG. 1 for bilirubin or could be bare nanoparticles to natively react with materials. Carron, et al., in U.S. Pat. No. 7,776,610 showed that native SERS active nanoparticles are capable of binding certain materials, such as cyanide or sulfur containing compounds, with very high sensitivity.

Figure 13:
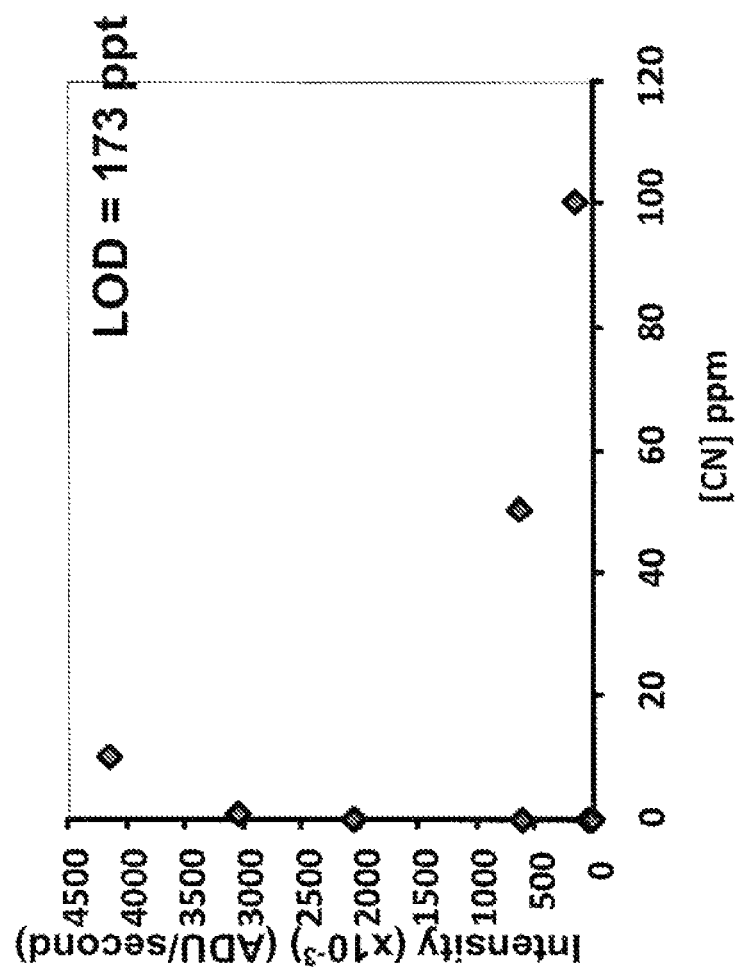
FIG. 13 illustrates a plot of cyanide intensity versus cyanide concentration.

In this implementation, motive particles (e.g., LDW, HDW or NDW particles) may be used as a direct assay when the nanoparticles themselves are the analyte binding reagent. Many materials will bind directly to gold. As an example, cyanide can act as an analyte which binds directly to gold. Its binding is illustrated in FIG. 12. The strength of the binding can be gauged by a plot of cyanide intensity versus the cyanide concentration. That is illustrated in FIG. 13 and from the plot we are able to determine a detection limit for cyanide of 200 parts per trillion.

Figure 14:
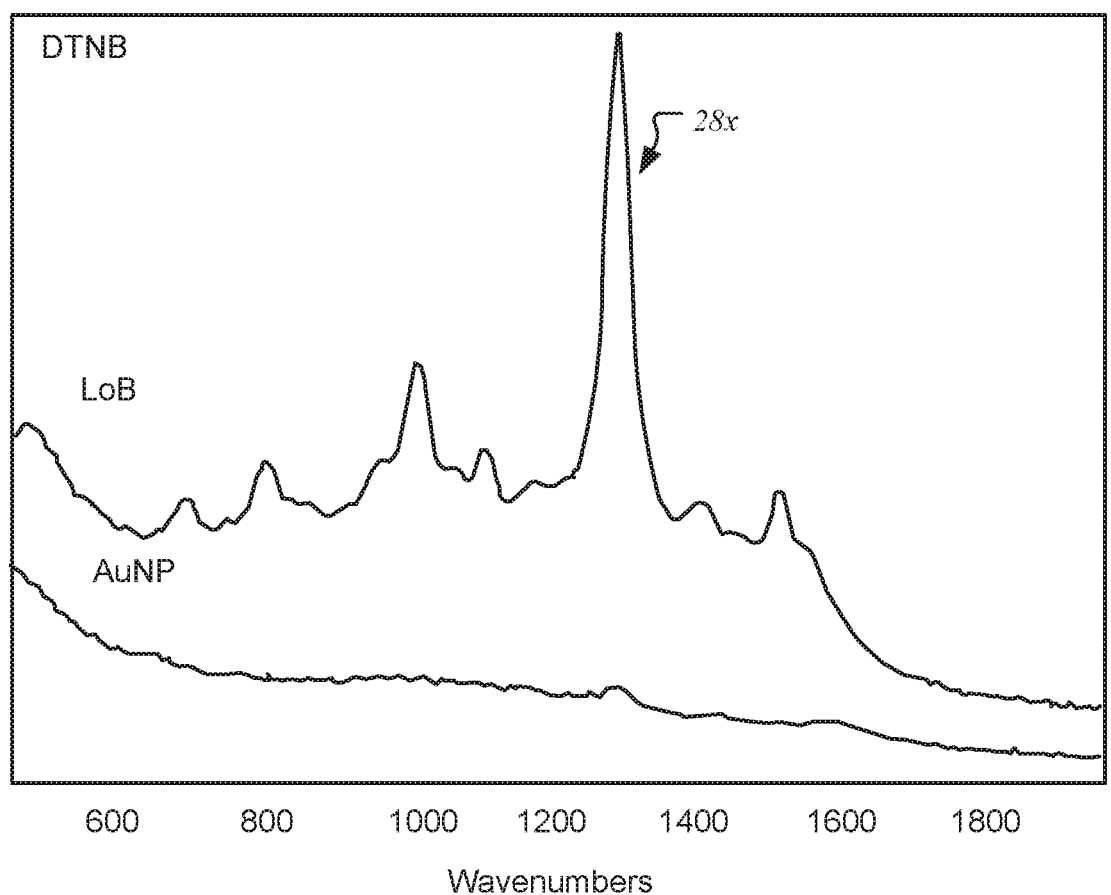
FIG. 14 illustrates spectra for a LDW particle which has a pre-aggregated nanoparticle coating and for an aggregation of nanoparticles from the same amount of analyte that exhibit a very weak signal.

Another important aspect of the motive particles is their aggregation of nanoparticles. It is well known that nanoparticle aggregates exhibit much larger Raman signals that individual nanoparticles. This can be explained by their electromagnetic properties. While aggregation leads to higher signal, it also causes nanoparticles to fall out of solutions and quickly destroys and assays results. However, larger motive particles, such as an LDW particle, are stable as the aggregation occurs during their formation and does not continue during the assay. This is illustrated in FIG. 14 with a popular assay reagent DTNB (5,5'-Dithio-bis(2-nitrobenzoic acid). The top spectrum is from a LDW particle which has a pre-aggregated nanoparticle coating; it has a strong signal. The lower spectrum is from the same amount of analyte and it exhibits a very weak signal due to aggregation of the nanoparticles.

As described above, the motive particles 62 (e.g., LDW particles) and/or the nanoparticle reporters (NPRs) 64 could be any number of different size particles. The motive particles 62, for example, could vary depending on the size of the sample. For example, ping pong ball sized or beach ball sized motive particles may be used in larger samples (e.g., within a pool or body of water) that could be easily collected from a surface of the sample.

Figure 6:
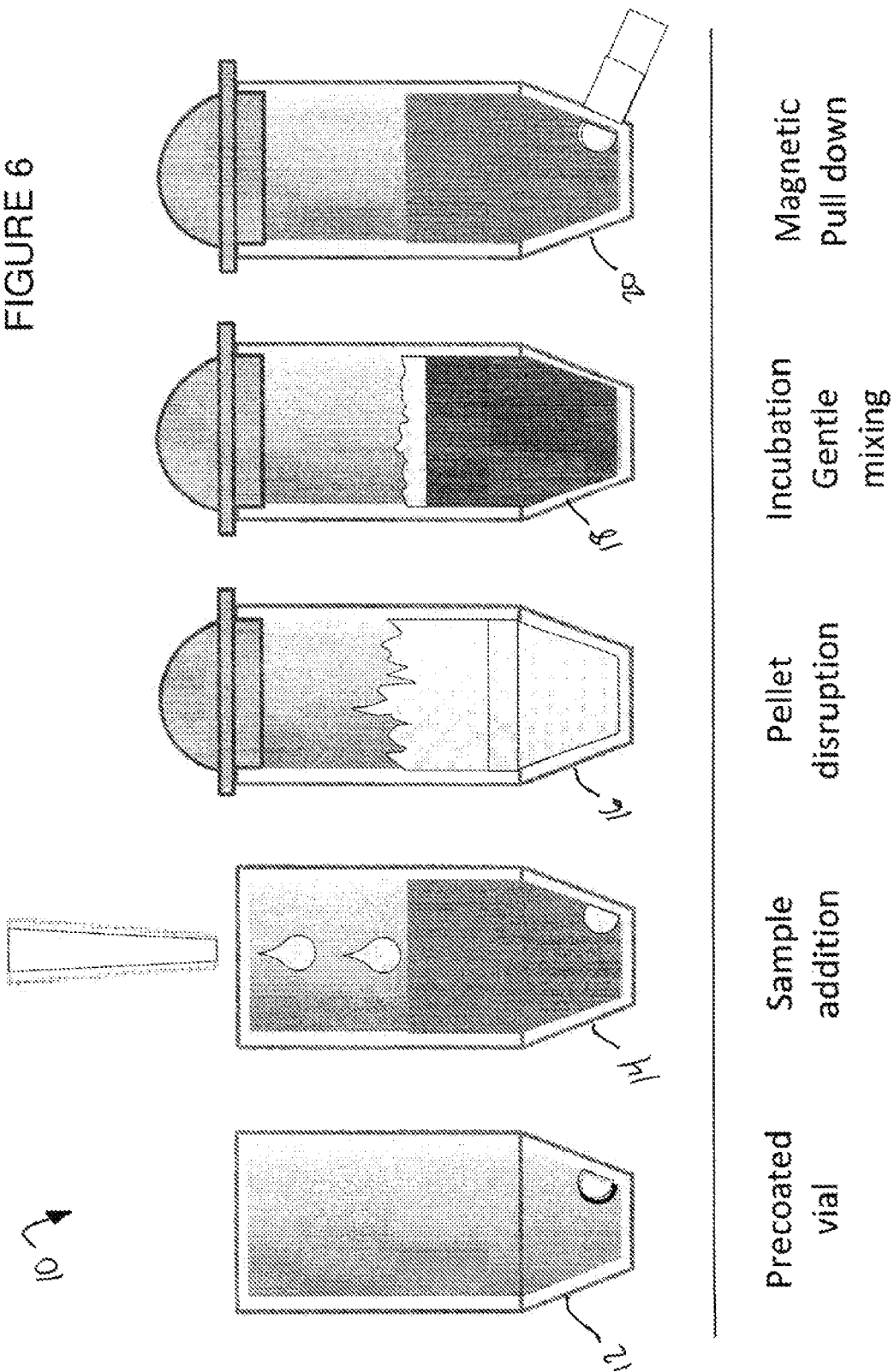
FIG. 6 illustrates steps of a complete paramagnetic pull-down assay.
Figure 7:
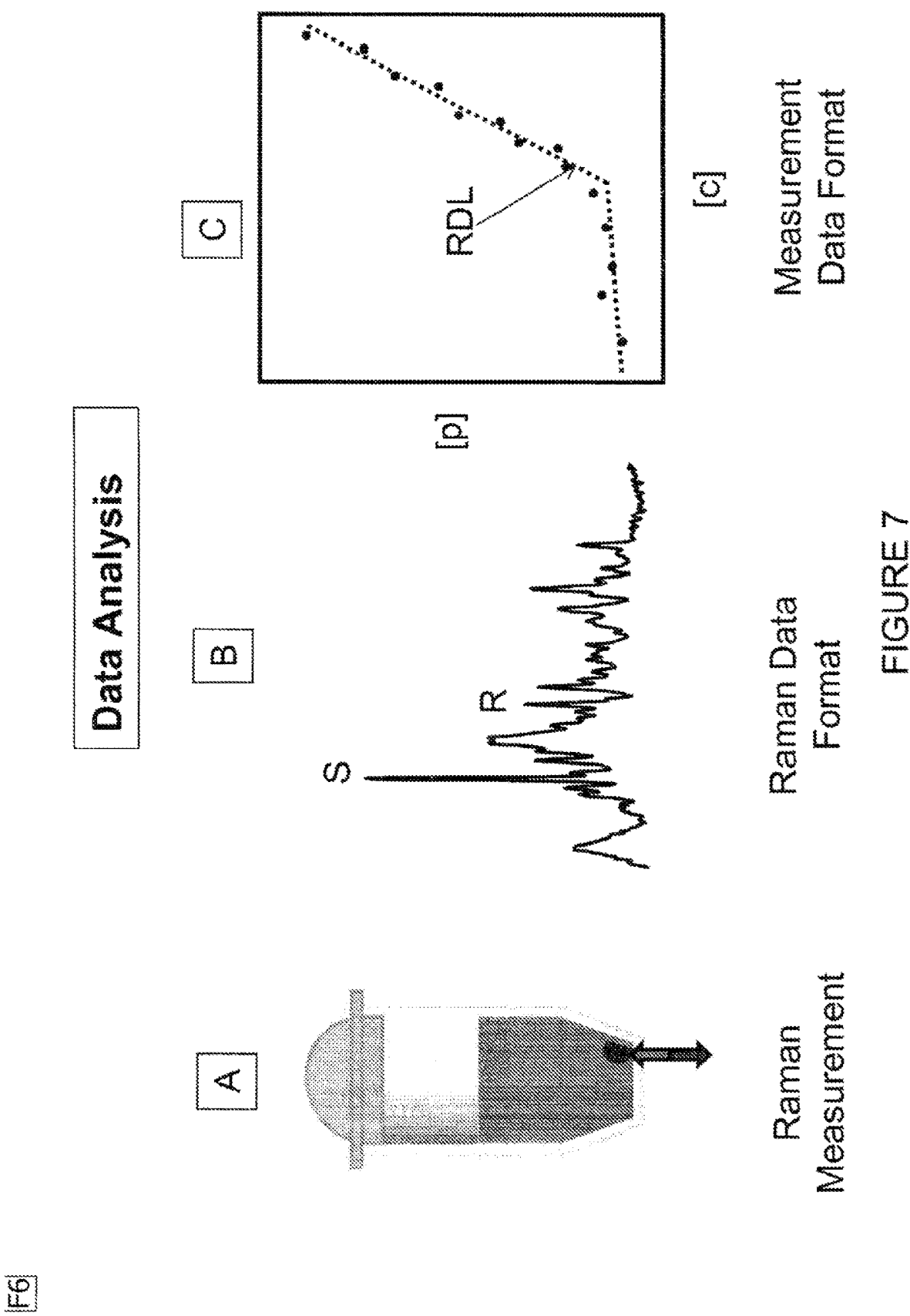
FIG. 7 illustrates a Raman measurement at label A, a Raman data format at label B and a measurement data format at label C pellet produced by a magnetic pull-down will only contain SERS active particles if the analyte is present to create the sandwich

Some advantages of the motive particles 32 shown in FIG. 8 include the simplicity of placing the SERS active LDW particles in samples, perhaps as large as bodies of water or water treatment facilities and later collection of the material floating on the surface. Equally simple and efficient is analysis in containers. In a container, the steps shown in FIG. 6 for a paramagnetic assay could be followed, with the exception of the last step. This exception leads to a significant advantage of this approach over a paramagnetic approach. Paramagnetism describes the magnetic attraction induced in a paramagnetic material by a magnet, such as a permanent magnet. The field produced by a magnet decreases rapidly as the distance from the magnet to the paramagnetic particle increases. The relationship is described by the inverse of the square of the distance. Assays developed around the paramagnetic concept suffer from long times required to pull the particles to a single point and from irreproducible pull-down. The distance squared relationship also greatly limits the sample size. Large samples cannot be tested due to the extremely long time required to pull-down the material.

FIGS. 15A through 15C show binding and separation events for an assay 70 including motive particles 72, such as LD motive particles, spectroscopic reporter particles 74 and a target analyte 76. In FIG. 15A, the motive particles 72, the spectroscopic reporter particles 74, and the target analyte 76 are present in a solution. The motive particles 72 and the spectroscopic reporter particles 74 each include analyte receptors 78, 80 for binding to the target analyte 76. FIG. 15B shows the motive particles 72 and the spectroscopic reporter particles 74 each bound to a target analyte 76 forming a completed sandwich assay. FIG. 15C shows the bound motive particles 72, spectroscopic reporter particles 74 and target analyte 76 undergoing a buoyant motive force to float to the top of the solution. In this implementation, spectroscopic reporters 74 that are not coupled to a motive particle 72, however, are denser than the surrounding solution and sink in the opposite direction from the motive particles 72 and the completed sandwich assay attached to the motive particles 72. As described below, an assay 70 may include a plurality of spectroscopic reporter particles 74 that are receptive to different target analyte particles 76 to provide a multiplex assay. Thus, if a particular target analyte 76 is not present in a sample solution, the corresponding spectroscopic reporter particles 74 will not bind to a motive particle 72 and can thus be easily separated from the particles to be interrogated by a spectrometer.

FIGS. 15D through 15F show an example assay using the components shown in FIGS. 15A through 15C. In FIG. 15D, a solution 82 is added to a container 84, such as a vial, test tube or the like, containing a plurality of motive particles 72 and spectroscopic reporter particles 74. The particles 72, 74, for example, may be bound to one or more sides of the container 84. The particles 72, 74 may be released from the side of the container 84, for example, by the introduction of the sample solution to the container 84 and/or agitation/mixing of the sample solution within the container 84. FIG. 15E shows the solution 82 and the particles 72, 74 mixed or agitated within the container 84. As the solution and the particles 72, 74 are mixed or agitated, target analyte particles 76 in the solution 82 interact with the receptors 78, 80 on the particles 72, 74, respectively. The motive particles 72 and spectroscopic reporter particles 74 bind with target analyte particles 76 present in the solution 82 as shown above in FIGS. 15A through 15C. As the solution 82 settles, the motive particles 72 float and bring with them any spectroscopic reporter particles 74 bound to them via one or more target analyte particles 76. The spectroscopic reporter particles 74 that are not bound to the motive particles 72 via a target analyte particle 76 sink away from the motive particles 72 and the completed sandwich assay.

The container shown in FIGS. 15D through 15F includes a narrow end in which the floating motive particles 72, along with any attached target analyte particles 76 and spectroscopic reporter particles 74, gather together. The container 82 comprises a material through which a spectroscopic signal may interrogate the gathered particles and receive a return spectroscopic signal from the particles. The container 84, for example, may be formed of a material that allows an interrogation signal and a return spectroscopic signal to pass through a wall of the container 84 or the container 84 may include a window through which a spectroscopic measurement may be taken.

The spectroscopic reporter particles 74 provide a strong spectroscopic signal that can be distinguished from other signals in the solution. Thus, where spectroscopic reporter particles 74 are bound to motive particles 72 in an area of the container 84 being interrogated, a spectrometer can detect the spectroscopic reporter particles 74 indicating the presence of the target analyte 76.

Figure 15:
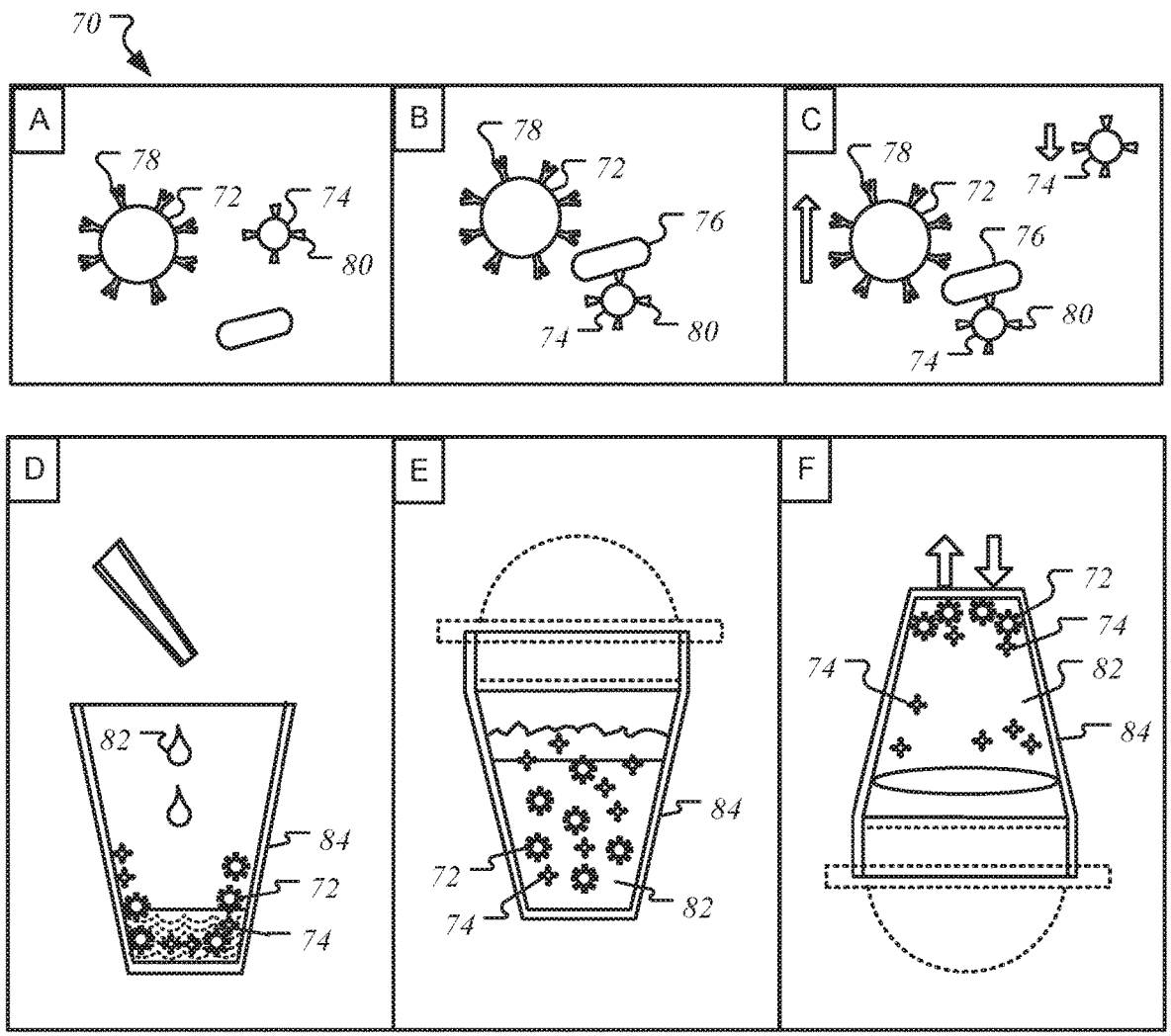
FIG. 15 shows binding and separation events for an assay including motive particles: spectroscopic reporter particles and a target analyte (labels A through C) and, in labels D through F, an example assay using the components shown.

In the particular implementation shown in FIGS. 15D through 15 F, for example, the container 84 has tapered side walls that narrow toward the bottom of the container 84. When the container 84 is turned upside down, the floating motive particles 72, along with any particles attached to those motive particles 72, gather together in the narrow bottom of the container 84 where they may be more easily interrogated by a spectrometer. In one implementation, sidewalls of the container may be treated with one or more surfactants to prevent the particles 72, 74 from sticking to the sidewalls when the container 84 is turned upside down. Although FIGS. 15A through 15F show floating motive particles 72 and sinking spectroscopic reporter particles 74, the motive particles 74 may instead sink or be neutral density and the spectroscopic reporter particles 74 may float or remain neutrally buoyant to separate from the motive particles 72.

The spectroscopic reporter particles 74 may be adapted for any type of spectroscopy, such as Raman or luminescence spectroscopy (e.g., fluorescence, phosphorescence, chemiluminescence spectroscopy) and the spectroscopic reporter particles 74 can be detected using any type of spectroscopy. Although particular types of spectroscopy are described as examples (e.g., Raman and fluorescence), these are merely examples of spectroscopy that may be used in a similar manner to interrogate spectroscopic reporter particles as described herein.

Figures 16A, 16B:
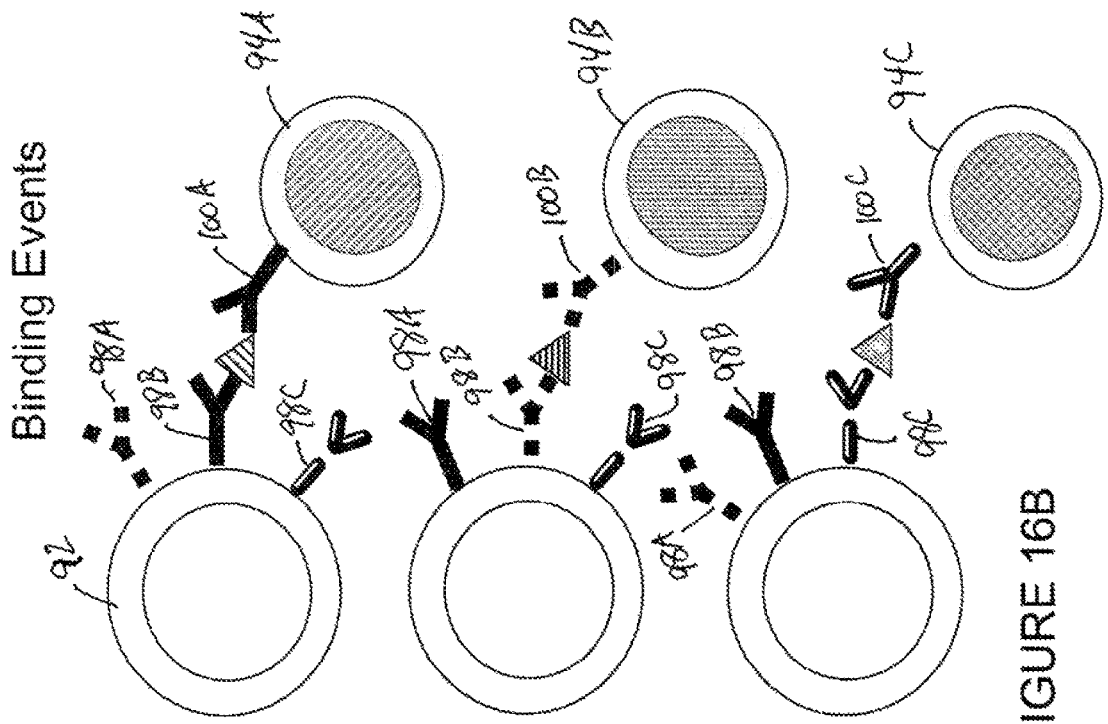
FIGS. 16A and 16B show an implementation of a multiplex assay including a motive particle and a plurality of different reagent spectroscopic reporter particles.

FIGS. 16A and 16B show an implementation of a multiplex assay 90 including a motive particle 92 and a plurality of different reagent spectroscopic reporter particles 94A, 94B, 94C. In this particular implementation, the motive particle 92 includes a plurality of receptors 98A, 98B, 98C that bind to different target analyte particles 96A, 96B, 96C (e.g., antigen or antibody particles). Alternatively, different motive particles 92 may bind to one or more different target analyte particles.

In this implementation, the motive particle 92 includes a first receptor 98A specific to a first target analyte 96A, a second receptor 98B specific to a second target analyte 96B, and a third receptor 98C specific to a third target analyte 96C. Although three different receptors are shown, any number of receptors may be used to correspond to any number of target analyte particles.

Each type of spectroscopic reporter particle 94 provides a unique spectroscopic signature that can be distinguished from the spectroscopic signatures of the other types of spectroscopic reporter particles. The different types of spectroscopic reporter particles also include different receptors specific to different target analyte particles (e.g., antigens or antibodies) to be detected in the multiplex assay. Thus a first reagent spectroscopic reporter particle 94A includes a first receptor 100A specific to the first target analyte 96A. A second reagent spectroscopic reporter particle 94B includes a second receptor 100B specific to the second target analyte 96B, and the third reagent spectroscopic reporter particle 94C includes a third receptor 100C specific to the third target analyte 96C.

FIG. 16B shows a binding event for the multiplex assay 90 of FIGS. 16A and 16B. In FIG. 16B, a plurality of motive particles 92 each having receptors 98A, 98B, 98C bind to different target analyte particles 96A, 96B, 96C via the respective receptors 98A, 98B, 98C. The spectroscopic reporter particles 94A, 94B, 94C, in turn, bind to the respective target analyte particles 96A, 96B, 96C via receptors 100A, 100B, 100C. Although FIG. 16B shows each motive particle bound to a single type of target analyte via the receptors 98A, 98B, 98C, each motive particle 92 can bind to different types of target analytes via its different receptors 98A, 98B, 98C, which in turn connect to different spectroscopic reporter particles 94A, 94B, 94C.

Figure 17:
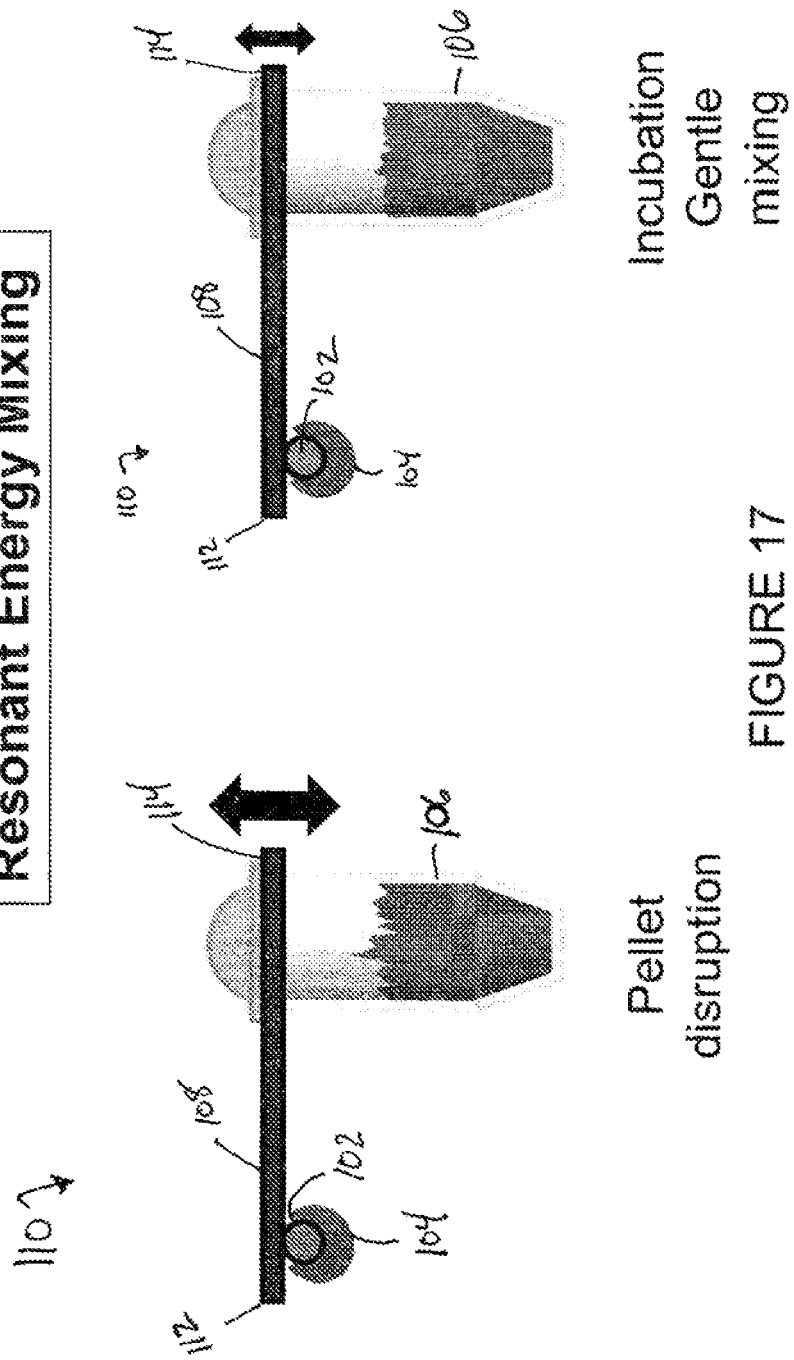
FIG. 17 illustrates an example mixer to resonantly mix materials in a container, such as a vial.

FIG. 17 illustrates an example mixer 110 to resonantly mix materials in a container, such as a vial. The approach shown in FIG. 17 uses motor 102 having an offset weight 104, such as a low power cell phone vibrating motor, to resonantly mix the materials in the container 106. A mixer 110 further comprises a flexible beam 108 that is anchored at a first location (e.g., at a proximal end 112 of the beam 108 or a location offset from the proximal end 112 of the beam 108). The flexible beam 108, for example, may comprise any relatively flexible material. In one implementation, for example, the flexible beam may comprise a ⅛" or 3/32" tube of polystyrene. Other relatively high modulus materials (e.g., brass or a helical steel spring) that are able to vibrate without unduly absorbing energy may also be used.

The container 106, such as a vial or test tube, holding a sample may be placed at a location offset from the anchored location of the flexible beam 108 (e.g., at a distal end 114 of the flexible beam 108 or offset from the distal end of the beam), where motion of the beam 108 can agitate the contents of the container 106.

The motor 102 is also disposed at a point along the flexible beam 108. Although the motor 102 is shown in FIG. 17 disposed on the bottom of the flexible beam 108 between the anchor point 112 of the beam 108 and the container 106, the motor 102 may be disposed in any location that allows the motor 102 to move the flexible beam 108 and, in turn, move the container 106 to agitate the contents of the container 106.

In one implementation, for example, the mixer can be designed to produce a mechanical resonance to efficiently mix the contents of the container. By placing the sample on a flexible arm of a length and shape to produce a mechanical resonance, for example, the sample can be mixed efficiently with low electrical power.

Figure 18A:
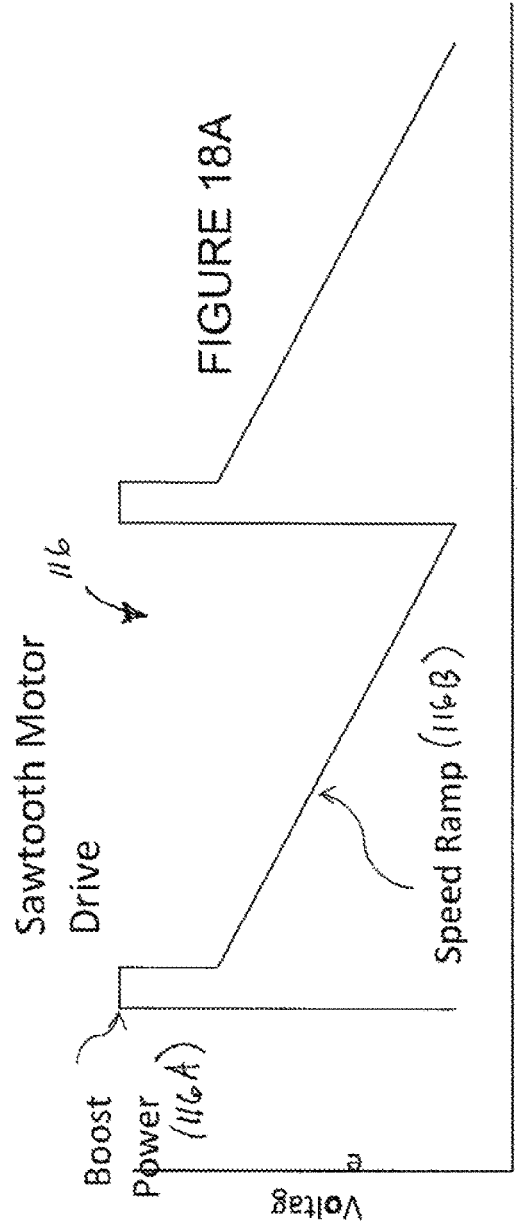
FIGS. 18A and 18B show waveforms of example motor drive signals that may be used to control a motor in the resonant mixer shown in Figure 17.
Figure 18B:
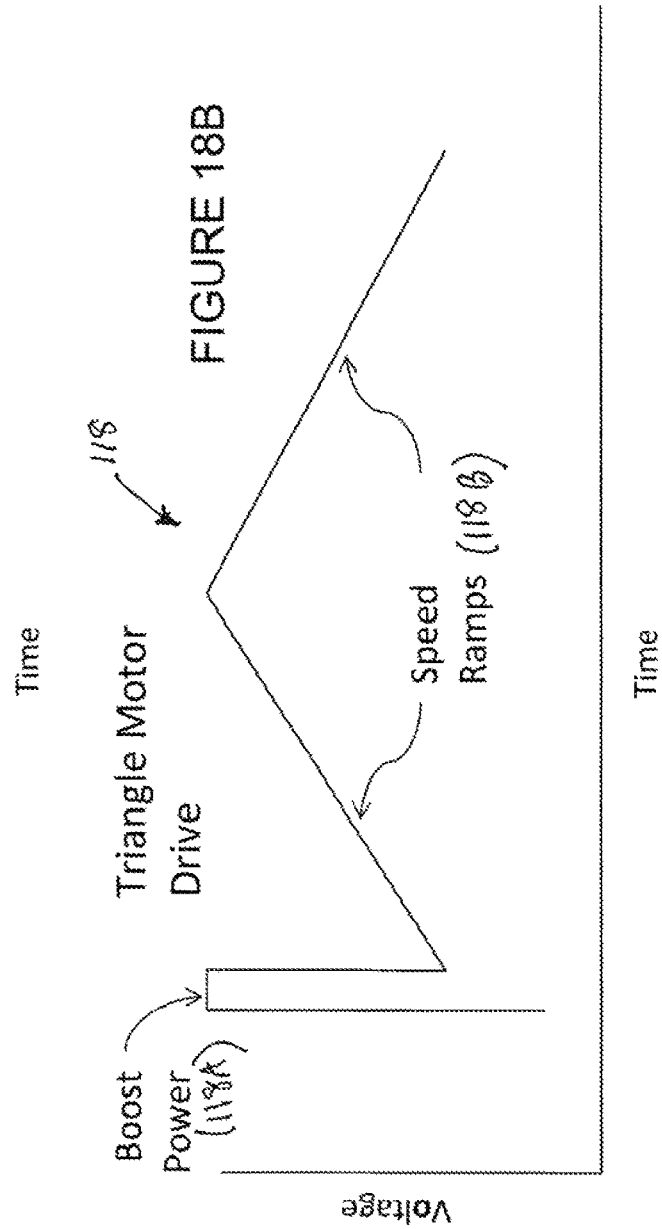

FIGS. 18A and 18B show waveforms of example motor drive signals that may be used to control a motor in the resonant mixer 110 shown in FIG. 17. FIG. 18A, for example, shows a sawtooth motor drive waveform 116 that may be used as a control signal for a motor 102 of a resonant mixer 110. The sawtooth motor drive waveform includes an initial power boost portion 116A and a speed control ramp portion 116B. FIG. 18B shows a triangle motor drive waveform 118 that may also be used as a control signal for a motor of the actuator assembly. The triangle motor drive waveform 118 includes an initial power boost portion 118A and a speed control ramp portion 118B. These example waveforms may be used to vary a motor speed in a controlled fashion. Since DC motors run at a lower speed (or voltage) than they will start at, a control signal may provide an initial spike and then switch to a controlled ramp signal.

In one implementation, LD motive particles all provide the same buoyant forces to drive them to the top of a sample. If the sample were a cone topped container, such as shown in FIGS. 15D through 15F, then they can be forced into a small concentrated area with the same benefits found for the paramagnetic pull-down assay, but with the added benefit of rapid separation that is not dependent on the square of the distance from a magnet or the need for an external actuator to gather them.

Figure 20:
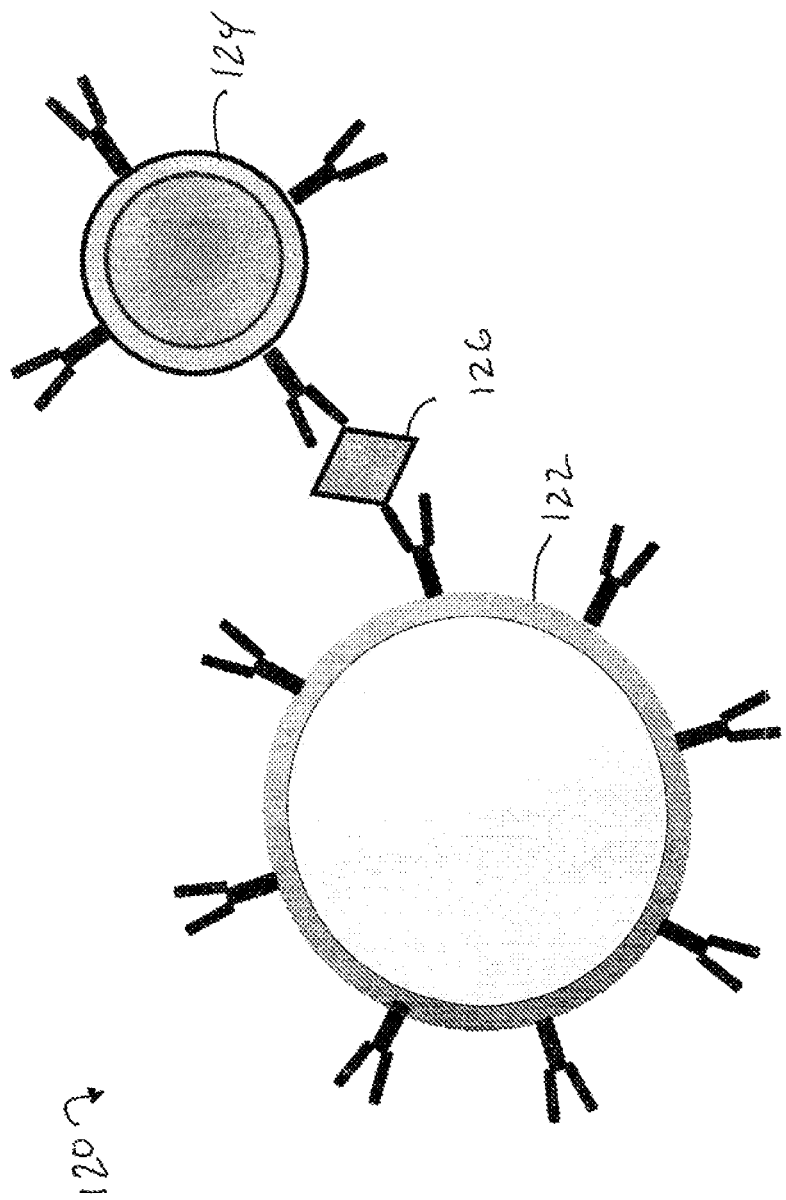
Figure 21:
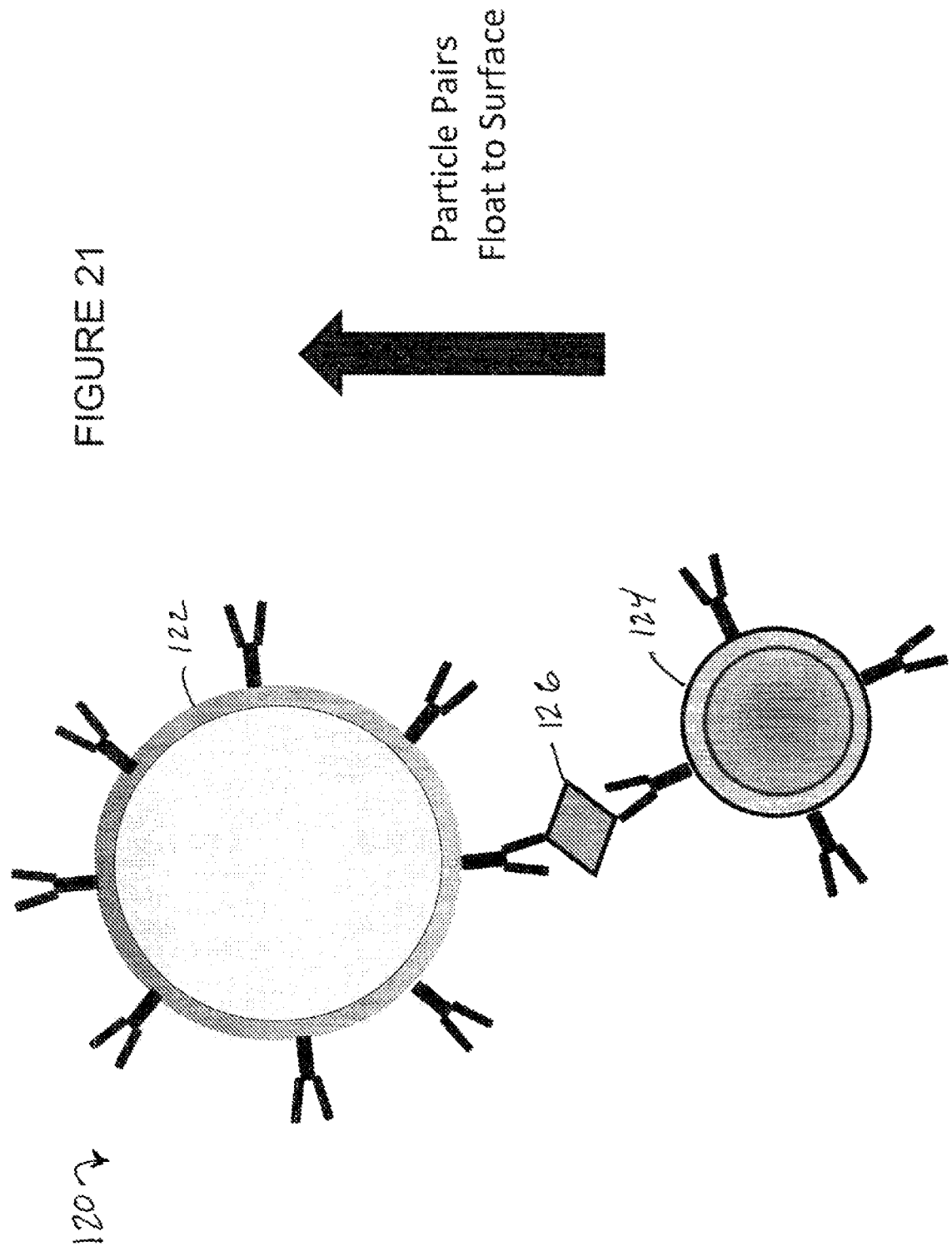
FIG. 21 shows an LDW-analyte-SERS active particle sandwich floating to the surface of a sample.

In one implementation, a sandwich assay 120 is provided. The assay, for example, may be equivalent in principle to that described in FIG. 5, using the concept and benefits of LDW particles 122. FIGS. 19 and 20 illustrate the equivalency between the LDW concept and the paramagnetic pull-down. In this case, a paramagnetic particle is replaced with an LDW motive particle 122. Surface modification is equivalent with an analyte specific coating. FIG. 21 shows an LDW-analyte-SERS active particle sandwich 120 floating to the surface of a sample. The sandwich includes the LDW motive particle 122 bound to a target analyte 126 via an analyte reagent coating on the particle 122 and a SERS active reporter particle 124 also bound to the target analyte via an analyte reagent coating on the particle 124.

Figure 22:
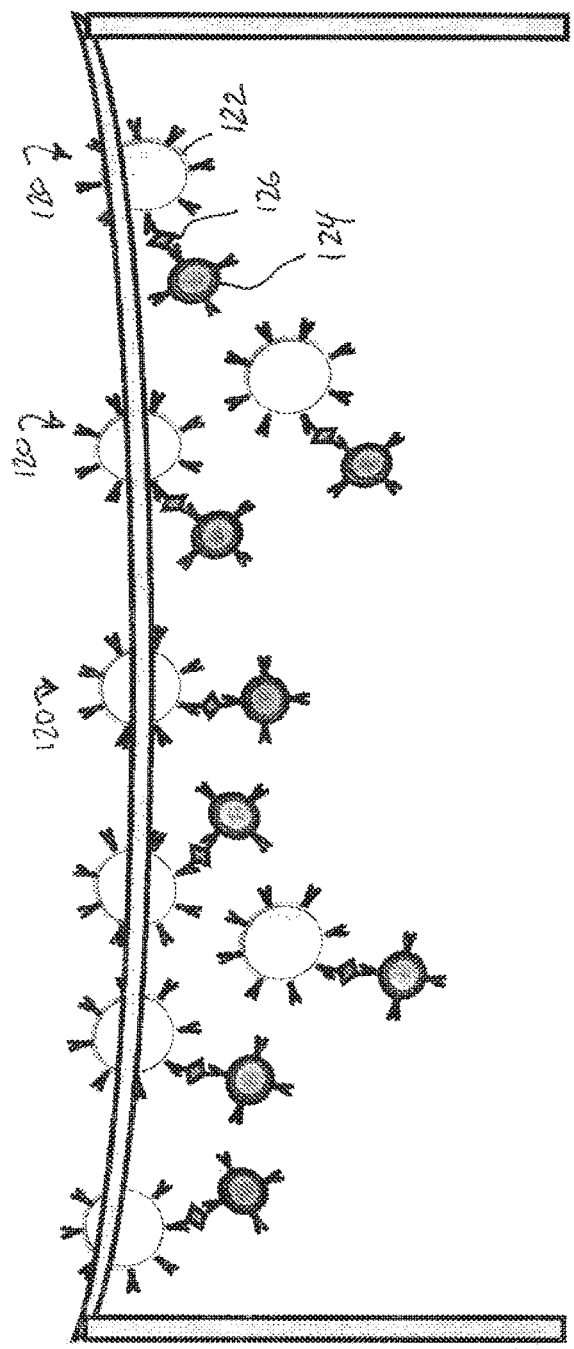
FIG. 22 illustrates that, after mixing, an LDW motive particle will act as an engine to pull a positive assay sandwich to the surface of a sample (or an HDW particle will pull the positive assay to the bottom of the sample).

FIG. 22 illustrates one benefit of this implementation over the paramagnetic method. As in FIG. 6, all of the steps would be followed, with the exception of the last step—the magnetic pull-down. FIG. 22 illustrates that after mixing an LDW motive particle will act as an engine to pull a positive assay sandwich 120 to the surface of the sample (or an HDW particle will pull the positive assay to the bottom of the sample). Unlike the paramagnetic case, the motive force for this particle engine is equivalent throughout the sample, not inversely related to the square of the distance from a magnet. Further, an additional actuator is not required to co-locate the positive assay sandwich.

Figure 4:
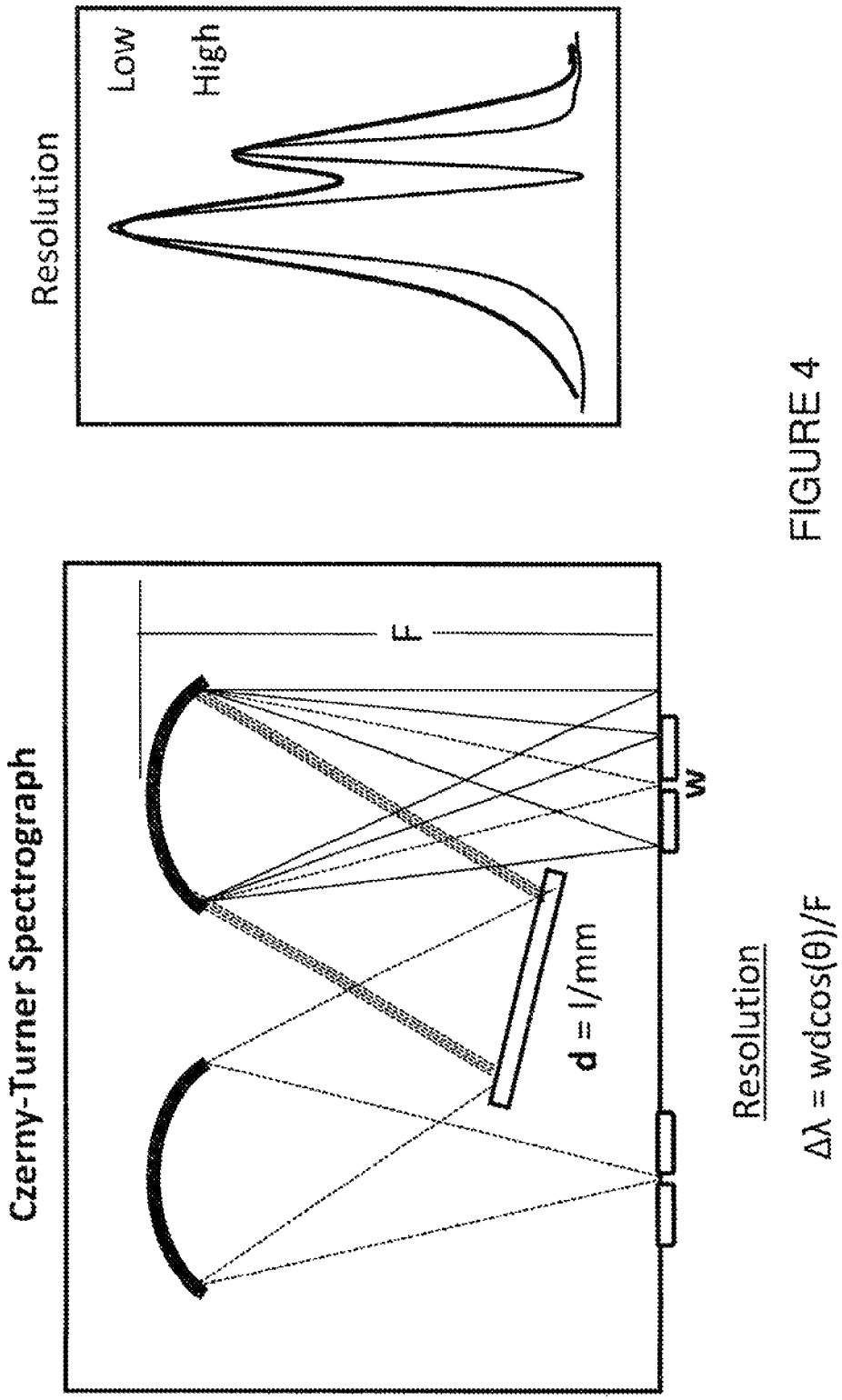
FIG. 4 illustrates that the size of a laser beam is related to the spectral resolution of a spectrometer.
Figure 23:
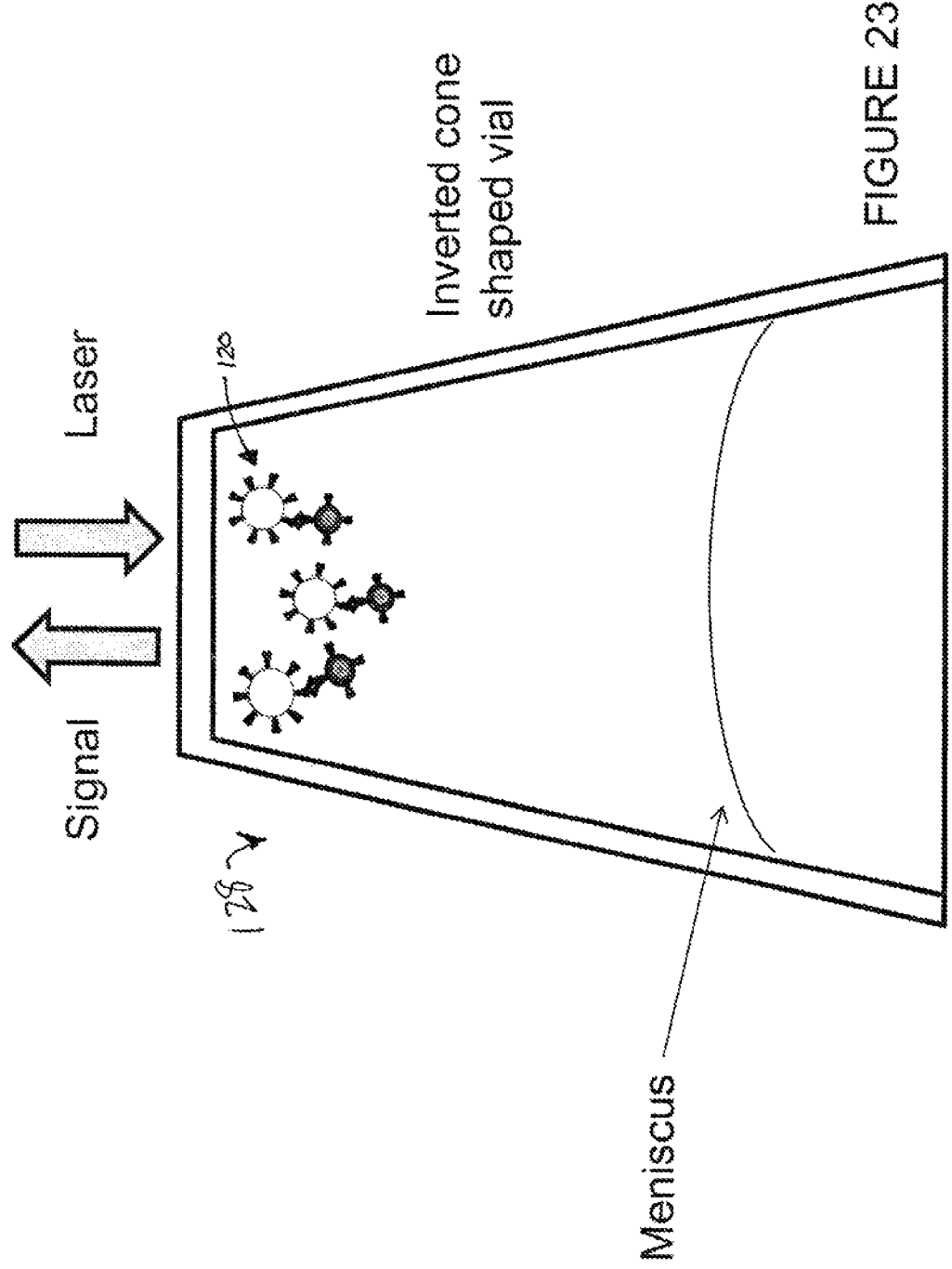
FIG. 23 shows a positive assay at a surface of a sample vial.

FIG. 23 illustrates how a positive assay might look at the surface of a sample vial. If the vial shape is cone shaped, as shown in FIGS. 14 and 15, the results can be concentrated to a small area and have the same advantages of separation for the sample's interfering elements and small point for good spectral resolution, as discussed with respect to FIG. 4, as are found with a paramagnetic pull-down. FIG. 23 shows an inverted cone shape vial 128, similar to the one shown in FIGS. 15D through 15F. As described above, a positive assay sandwiches 120 may be co-located at a common location within the vial where a spectrometer may detect the spectroscopic reporter particles 124 of the positive assay sandwich 120.

Figure 24A:
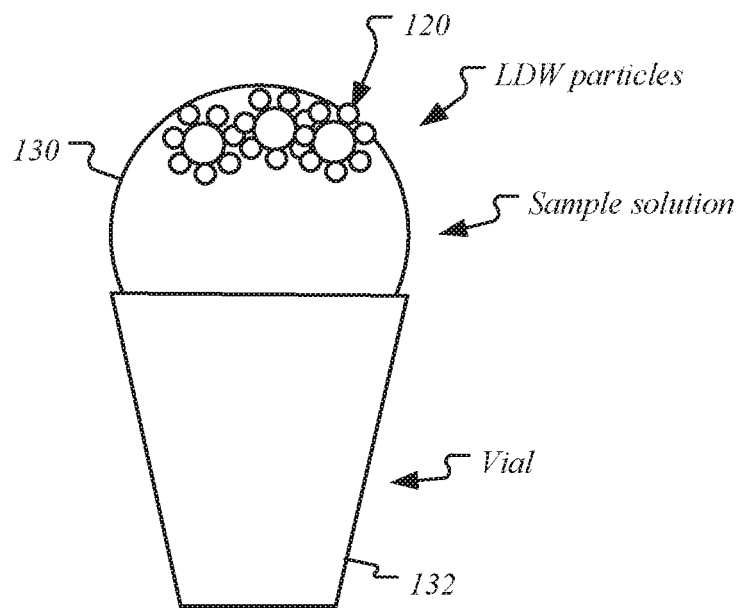
FIGS. 24A and 24B show two methods of sampling using a natural convex shape produced by a droplet.
Figure 24B:
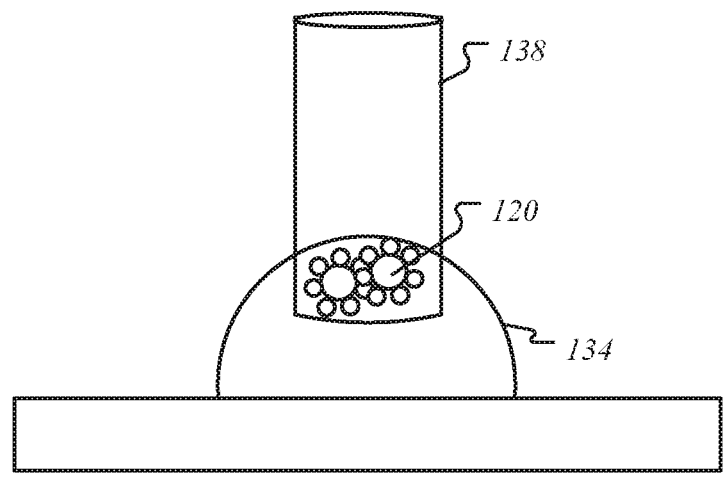

FIGS. 24A and 24B show two methods of sampling using the natural convex shape produced by a droplet. The convex shape creates a natural focusing effect to collect the LDW particles. It can be seen that the laser beam is able to easily interrogate all of the particles with this configuration. FIG. 24A, for example, shows an implementation in which the positive sandwich assays 120 and motive particles 122 float to the top of the natural convex shape produced by a liquid sample 130 overflowing a container 132. The container 132, for example, may comprise a well of an assay well plate in which the sample solution is filled to a point where the convex shape forms over the top of the container 132.

FIG. 24B shows a droplet 134 of a sample solution, such as placed on a substrate 136. Similar to the solution shown in FIG. 24A, positive sandwich assays 120 float to the top of the natural convex shape formed by the droplet 134 of the sample solution disposed on the substrate 136.

In both the implementations shown in FIGS. 24A and 24B, a spectrometer incident beam 138 may be used to detect the presence or absence of a positive sandwich assay floating at the top of the droplets.

Figure 25:
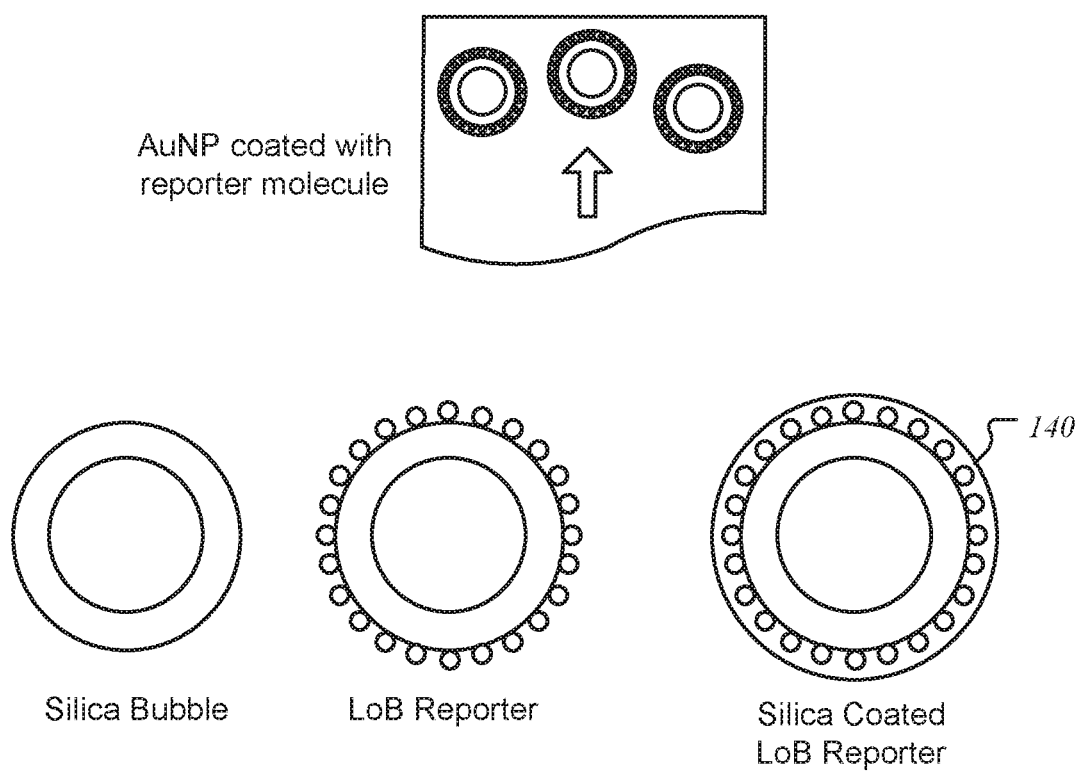
FIG. 25 shows an example of a taggant particle.

FIG. 25 shows an example of a taggant particle 140. The taggant particle 140, for example, may comprise a floating, sinking or neutral weight particle used to tag a particular liquid. The taggant particle 140, for example, may be used to identify an authentic product or tag a particular type of liquid product. A taggant particle, for example, may identify a source of a particular liquid product (e.g., an oil or gasoline product) that can be verified at a later time. In this manner, the taggant particles 140 can be used to ensure that a solution has not been replaced, diluted, or the like.

In the implementation shown in FIG. 25, for example, the taggant particle 140 is formed from a silica bubble to provide a floating taggant particle 140. Where sinking or neutral buoyancy particles are desired, a solid or lesser internal bubble portion may be used to tailor the density of the particle for a particular use. SERS active nanoparticles (e.g., gold, silver, or copper nanoparticles) are coated onto a surface of the silica bubble forming a Lab on a Bubble (LoB) reporter particle. A reporter molecule can be bound to the SERS active nanoparticles to provide a particular spectroscopic signature for the taggant particle 140. As discussed above, for example, gold nanoparticles can directly bind to a number of reporter molecules, or the particular reporter molecule may be coupled indirectly to the silica bubble and/or the SERS active nanoparticle coating on the bubble particle. A protective silica coating is then formed over the silica bubble and SERS active nanoparticle coating to protect the taggant particle 140 and to prevent the spectroscopic signature of the taggant particle 140 from being altered.

Although FIG. 25 shows a process of forming a taggant particle, similar steps may be taken to form a motive particle or spectroscopic reporter particle of a sandwich assay as described in detail above.

Figure 26:
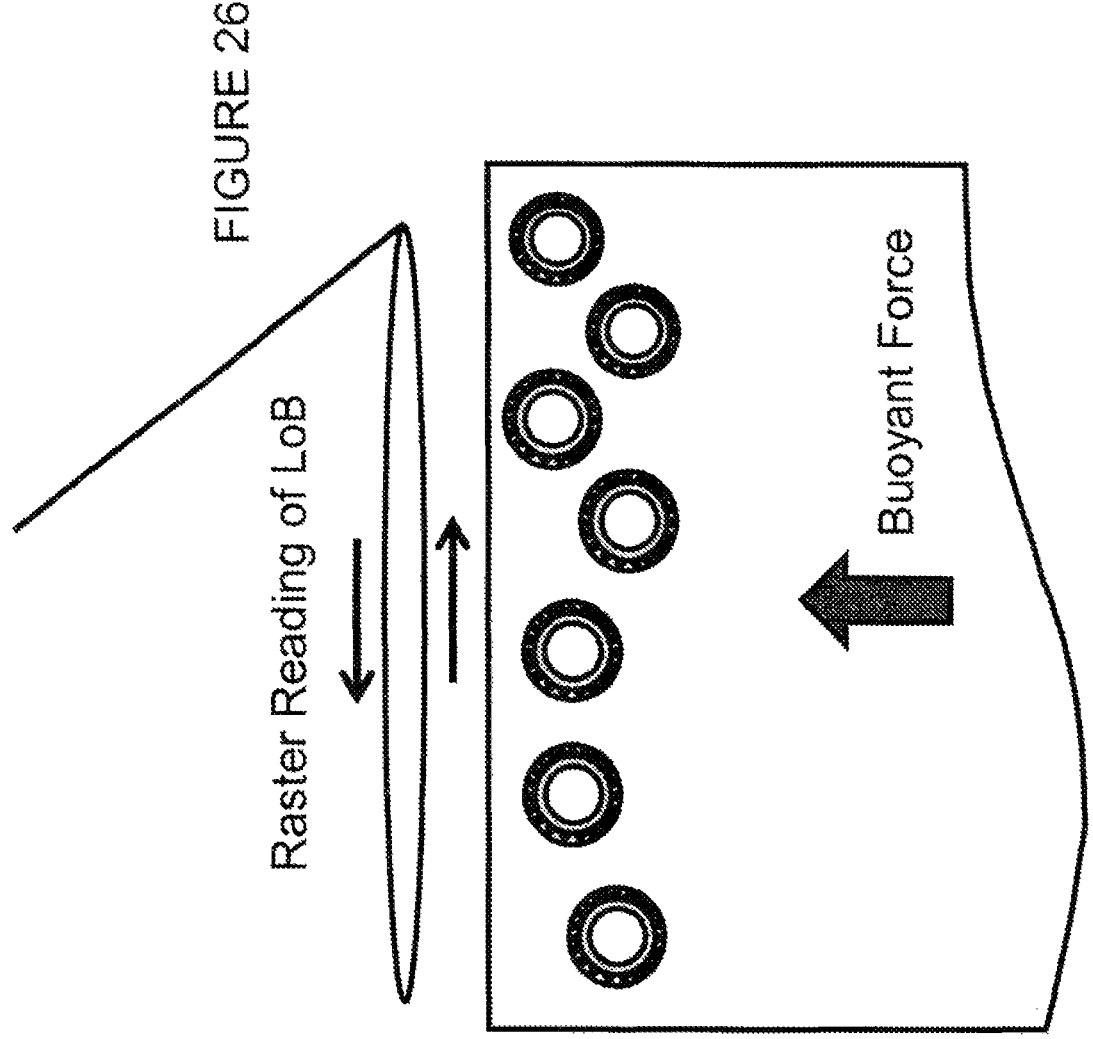
FIG. 26 shows an example spectrometer interrogation of a plurality of assay particles co-located within a sample.

FIG. 26 shows an example spectrometer interrogation of a plurality of assay particles co-located within a sample. In the implementation of FIG. 26, the motive particles of a sandwich assay have been used to separate and concentrate one or more positive sandwich assays into a single location, such as at an edge of a solution. A spectrometer can detect the presence or absence of a positive sandwich assay As described below, by moving an incident beam of a spectrometer across the sample, the spectrometer can detect spectroscopic reporter particles that may be attached to the plurality of motive particles gathered together in the assay. The spectrometer can move a focused incident beam (e.g., a focused laser beam) across the surface of the sample to generate a relatively large focal area of the spectrometer with respect to the size of the focused beam. The focused beam can be moved across the surface of the sample in any path or pattern in a controlled or uncontrolled manner, such as by moving a reflective mirror of the spectrometer in any number of ways. In this manner, the spectrometer can sample a large focal area without losing resolution due to the de-focusing of the incident beam on the sample. Thus, the spectrometer is able to interrogate a large area with a high resolution to effectively distinguish between a plurality of reporters, such as in a multiplex assay. One example spectrometer is discussed in detail in U.S. patent application Ser. No. 13/221,899, entitled "Spectrometer" and file on Aug. 30, 2011 by Watson et al. and in U.S. provisional application No. 61/450,123 filed on Mar. 7, 2011, each of which applications are incorporated herein in their entirety as if fully set forth herein.

Figure 27:
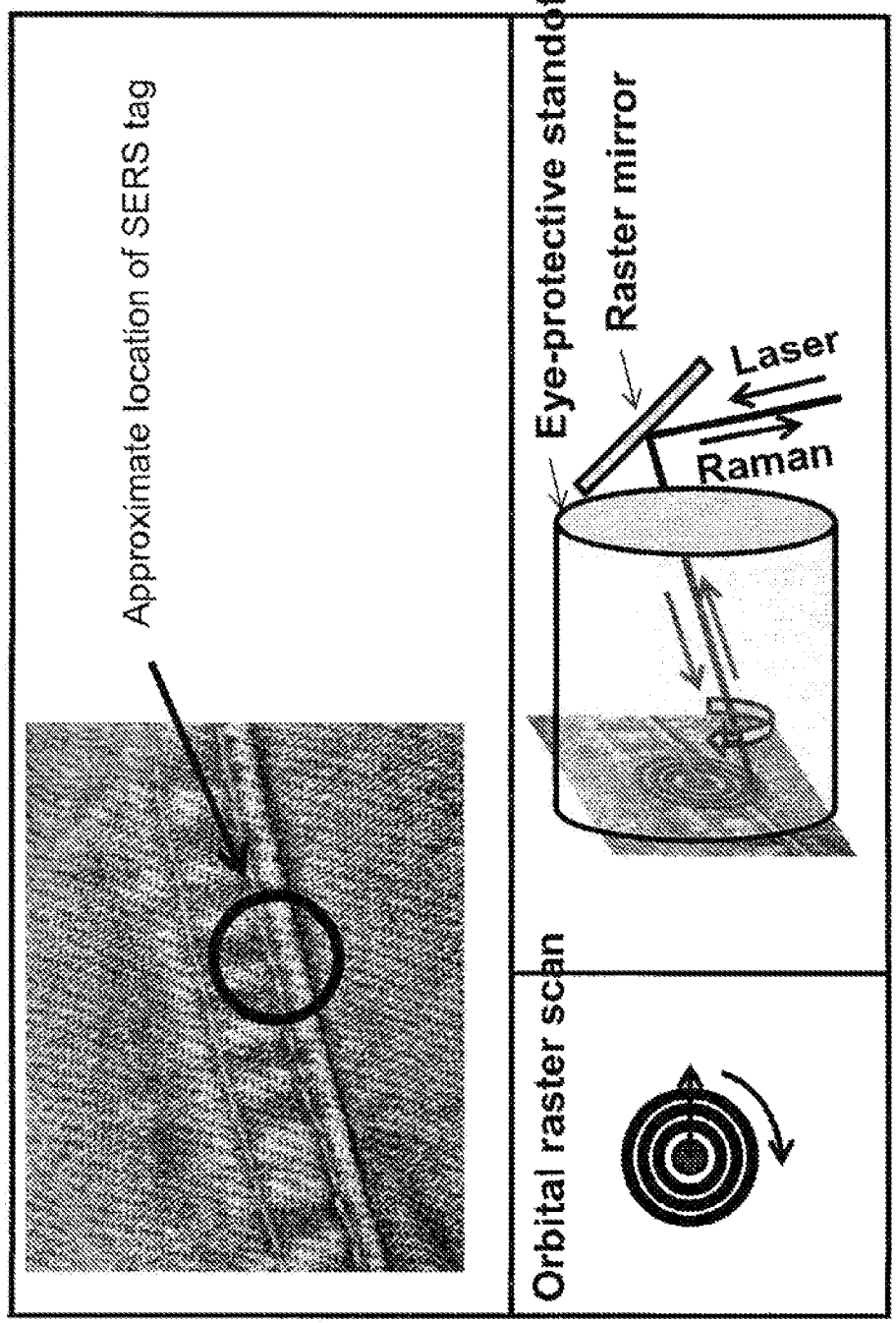
FIG. 27 shows an example orbital raster scan that may be used by a spectrometer, such as a Raman or luminescence spectrometer, to interrogate an area of a target for a spectroscopic reporter particle.

FIG. 27 shows an example orbital raster scan that may be used by a spectrometer, such as a Raman or luminescence spectrometer, to interrogate an area of a target for a spectroscopic reporter particle. As show in FIG. 27, the orbital raster scan can move the incident beam of a spectrometer across a surface of the sample to create an orbital raster pattern by moving a reflective raster minor. In addition, an eye-protective standoff can be used to reduce the likelihood of the incident beam escaping from the target sample.

Although embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of providing a spectroscopic assay comprising:
    providing a sample solution;
    introducing a motive particle comprising an internal bubble to the sample solution, the motive particle comprising a relatively lower density than the sample solution to provide buoyancy to the motive particle within the sample solution, the motive particle comprising a first analyte binding reagent for selectively binding to a target analyte;
    introducing a spectroscopic reporter particle that provides a predetermined spectroscopic signal in response to being interrogated by a spectrometer, the spectroscopic reporter particle comprising a second analyte binding reagent for selectively binding to the target analyte;
    mixing the motive particle and the spectroscopic reporter particle within the sample solution, wherein the motive particle and the spectroscopic reporter particle provide a sandwich assay in the presence of the target analyte via the first and second analyte binding reagents binding to the target analyte; and
    interrogating an area of the sample to determine whether the spectroscopic reporter particle is present.

2. The method of providing a spectroscopic assay of claim 1 wherein the motive particle provide buoyancy to the motive particle and a positive sandwich assay within the sample solution.

3. The method of providing a spectroscopic assay of claim 2 wherein the buoyancy of the motive particle provides a motive force to concentrate a plurality of positive sandwich assays within the sample solution.

4. The method of providing a spectroscopic assay of claim 2 wherein the plurality of positive sandwich assays are concentrated toward a top of the solution by floating motive particles.

5. The method of providing a spectroscopic assay of claim 4 wherein the spectroscopic reporter particles sink or remain neutrally buoyant within the sample solution.

6. The method of providing a spectroscopic assay of claim 1 wherein the spectroscopic reporter particles float or remain neutrally buoyant within the sample solution.

7. The method of providing a spectroscopic assay of claim 1 wherein the motive particle remains neutrally buoyant within the solution.

8. The method of providing a spectroscopic assay of claim 1 wherein the motive particle is relatively equally dense with the solution to provide a neutrally buoyant motive force to keep the motive particle and a positive assay sandwich in solution.

9. The method of providing a spectroscopic assay of claim 1 wherein the motive particle comprises a SERS active material bound to the motive particle to enhance a Raman spectroscopy interrogation.

10. The method of providing a spectroscopic assay of claim 1 wherein the motive particle comprises a plurality of SERS active nanoparticles bound to the motive particle.

11. The method of providing a spectroscopic assay of claim 10 wherein the plurality of SERS active nanoparticles are aggregated on a surface of the motive particle.

12. The method of providing a spectroscopic assay of claim 1 wherein the motive particle floats within the sample solution.

13. A method of providing a multiplex spectroscopic assay comprising:
providing a sample solution;
introducing a motive particle comprising an internal bubble to the sample solution, the motive particle comprising a relatively lower density than the sample solution to provide buoyancy to the motive particle within the sample solution, the motive particle comprising a first analyte binding reagent for selectively binding to a first target analyte and a second analyte binding reagent for selectively binding to a second target analyte; and
introducing a first spectroscopic reporter particle that provides a first predetermined spectroscopic signal in response to being interrogated by a spectrometer, the first spectroscopic reporter particle comprising a third analyte binding reagent for selectively binding to the first target analyte;
introducing a second spectroscopic reporter particle that provides a second predetermined spectroscopic signal differing from the first predetermined spectroscopic signal in response to being interrogated by the spectrometer, the second spectroscopic reporter particle comprising a fourth analyte binding reagent for selectively binding to the second target analyte;
mixing the motive particle, the first spectroscopic reporter particle and the second spectroscopic reporter particle within the sample solution, wherein the motive particle and the first spectroscopic reporter particle provide a first sandwich assay in the presence of the first target analyte via the first and third analyte binding reagents binding the first target analyte, and the motive particle and the second spectroscopic reporter particle provide a second sandwich assay in the presence of the second target analyte via the second and fourth analyte binding reagents binding the second target analyte; and
interrogating an area of the sample to determine whether at least one of the first spectroscopic reporter particle and the second spectroscopic reporter particle are present.

14. The method of providing a multiplex spectroscopic assay of claim 13 wherein the motive particle provides buoyancy to the motive particle and a positive sandwich assay within the sample solution.

15. The method of providing a multiplex spectroscopic assay of claim 13 wherein the motive particle floats within the sample solution.

* * * * *